United States Patent
Creighton et al.

(10) Patent No.: US 11,517,729 B2
(45) Date of Patent: Dec. 6, 2022

(54) INTEGRATED FIBER MICRONEEDLE DEVICE FOR DRUG AND VACCINE DELIVERY

(71) Applicants: Rachel Creighton, Seattle, WA (US); Kim Woodrow, Seattle, WA (US)

(72) Inventors: Rachel Creighton, Seattle, WA (US); Kim Woodrow, Seattle, WA (US)

(73) Assignee: University of Washington, Seattle, WA (US)

( * ) Notice: Subject to any disclaimer, the term of this patent is extended or adjusted under 35 U.S.C. 154(b) by 132 days.

(21) Appl. No.: 16/546,098

(22) Filed: Aug. 20, 2019

(65) Prior Publication Data

US 2020/0054870 A1 Feb. 20, 2020

Related U.S. Application Data

(60) Provisional application No. 62/719,812, filed on Aug. 20, 2018.

(51) Int. Cl.
*A61M 37/00* (2006.01)
*B29C 41/00* (2006.01)
(Continued)

(52) U.S. Cl.
CPC ........ *A61M 37/0015* (2013.01); *B29C 41/006* (2013.01); *A61M 2037/0023* (2013.01);
(Continued)

(58) Field of Classification Search
CPC ...... A61M 37/0015; A61M 2037/0053; A61M 2037/0023; A61M 2037/0046;
(Continued)

(56) References Cited

U.S. PATENT DOCUMENTS

| 8,366,677 B2 | 2/2013 | Kaspar et al. |
| 8,986,256 B2 | 3/2015 | Scholten et al. |

(Continued)

FOREIGN PATENT DOCUMENTS

| CN | 106581777 | 4/2017 |
| CN | 108030775 | 5/2018 |

(Continued)

OTHER PUBLICATIONS

Moronkeji et al, "The role of subcutaneous tissue stiffness on microneedle performance in a representative in vitro model of skin", J Control Release, 265, 102-112 (2017).

(Continued)

*Primary Examiner* — Amber R Stiles
(74) *Attorney, Agent, or Firm* — McDonnell Boehnen Hulbert & Berghoff LLP

(57) ABSTRACT

Systems and methods are provided for fabricating microneedle arrays that includes electrospun fibers preferentially disposed within the microneedles of the array. Providing the electrospun fibers preferentially in the microneedles allows for more of a drug or other substance present in the fibers to be deposited into tissue or to provide other benefits. A mold for forming the microneedle arrays includes an insulating surface layer. The insulating surface layer affects the electric field during electrospinning such that electrospun fibers are deposited preferentially within the microneedle cavities of the mold relative to the surface of the mold. A bulk material can then be applied to the mold to form the bulk of the microneedles with electrospun fibers embedded within and a backing layer to which the microneedles are attached.

8 Claims, 11 Drawing Sheets

(51) Int. Cl.
| | |
|---|---|
| B29K 105/00 | (2006.01) |
| B29L 31/00 | (2006.01) |
| B29K 83/00 | (2006.01) |
| D01D 5/00 | (2006.01) |

(52) U.S. Cl.
CPC .. *A61M 2037/0053* (2013.01); *B29K 2083/00* (2013.01); *B29K 2105/0035* (2013.01); *B29K 2105/0073* (2013.01); *B29L 2031/756* (2013.01); *B29L 2031/7544* (2013.01); *D01D 5/0007* (2013.01)

(58) Field of Classification Search
CPC ............... B29C 41/006; B29C 39/025; B29K 2105/0073; B29K 2083/00; B29K 2105/0035; B29L 2031/756; B29L 2031/7544; D01D 5/0007; D01D 5/0076
See application file for complete search history.

(56) References Cited

U.S. PATENT DOCUMENTS

| | | | |
|---|---|---|---|
| 9,302,903 | B2 | 4/2016 | Park et al. |
| 2007/0161964 | A1* | 7/2007 | Yuzhakov ......... A61M 37/0015 604/272 |
| 2009/0182306 | A1* | 7/2009 | Lee ...................... B29C 41/04 604/506 |
| 2010/0228203 | A1* | 9/2010 | Quan ................ A61M 37/0015 604/272 |
| 2011/0009782 | A1* | 1/2011 | Pampalone ........ A61H 15/0092 601/119 |
| 2011/0098651 | A1 | 4/2011 | Falo et al. |
| 2014/0128345 | A1 | 5/2014 | Woodrow et al. |
| 2014/0142541 | A1 | 5/2014 | Yan et al. |
| 2014/0200509 | A1 | 7/2014 | Cohen et al. |
| 2015/0126633 | A1* | 5/2015 | Jung ...................... C08J 9/0061 521/134 |
| 2017/0189661 | A1 | 7/2017 | Lee |
| 2019/0153517 | A1 | 5/2019 | Li et al. |

FOREIGN PATENT DOCUMENTS

| | | |
|---|---|---|
| CN | 108525013 | 9/2018 |
| KR | 20100130502 | 12/2010 |
| KR | 101527469 | 6/2015 |
| KR | 20150138647 | 12/2015 |
| KR | 20170024951 | 3/2017 |
| MX | 2014013521 | 5/2016 |
| WO | WO 2009/094394 | 7/2009 |
| WO | WO 2018/226563 | 12/2018 |
| WO | WO 2019/103404 | 5/2019 |

OTHER PUBLICATIONS

Nejad et al, "Low-cost and cleanroom-free fabrication of microneedles", Microsystems & Nanoengineering 4, 17073 (2018).
Niu et al, Characterizing and Patterning of PDMS-Based Conducting Composites. Advanced Materials, 19, 2682-2686 (2007).
Olatunji et al, "Influence of Array Interspacing on the Force Required for Successful Microneedle Skin Penetration: Theoretical and Practical Approaches", Journal of Pharmaceutical Sciences, 102, 1209 (2013).
Ono et al, "Development of Novel Faster-Dissolving Microneedle Patches for Transcutaneous Vaccine Delivery", Pharmaceutics 3;9(3):27 (2017).
Park et al, "Biodegradable polymer microneedles: Fabrication, mechanics and transdermal drug delivery", Journal of Controlled Release, 104 (1), 51-66 (2005).
Park et al, "Polymer Microneedles for Controlled-Release Drug Delivery", Pharmaceutical Research 23(5), 1008-19 (2006).
Prausnitz, "Microneedles for transdermal drug delivery", Adv Drug Deliv Rev 56, 581-587, doi:10.1016/j.addr.2003.10.023 (2004).
Rujitanaroj et al, "Nanofiber-mediated controlled release of siRNA complexes for long term gene-silencing applications", Biomaterials, 32 (25), 5915-23 (2011).
Rutledge et al, "Formation of fibers by electrospinning", Advanced Drug Delivery Reviews 59, 1384-1391, doi:10.1016/j.addr.2007.04.020 (2007).
Ryu et al, "Role of Electrical Conductivity of Spinning Solution on Enhancement of Electrospinnability of Polyamide 6,6 Nanofibers", Journal of Nanoscience and Nanotechnology, 13 (6), 4193-4202 (2013).
Saraf et al, "Regulated non-viral gene delivery from coaxial electrospun fiber mesh scaffolds", Journal of Controlled Release 143, 95-103, doi:10.1016/j.jconrel.2009.12.009 (2010).
Schreuder-Gibson et al, "Protective textile materials based on electrospun nanofibers", Journal of Advanced Materials, 34 (3), 44-55 (2002).
Song et al, "Nanofibrous Microposts and Microwells of Controlled Shapes and Their Hybridization with Hydrogels for Cell Encapsulation", ACS Appl. Mater. Interfaces 6, 10, 7038-7044 (2014).
Stoddard et al, "In Pursuit of Functional Electrospun Materials for Clinical Applications in Humans", Ther Deliv. vol. 7(6): 387-409 (2016).
Sullivan et al, "Dissolving Polymer Microneedle Patches for Influenza Vaccination", Nat Med. 16(8): 915-920 (2010).
Sun et al, "Near-field electrospinning", Nano Letters, 6 (4), 839-842 (2006).
Thoppey et al, "Control of the electric field-polymer solution interaction by utilizing ultra-conductive fluids", Polymer 55, 6390-6398, doi:10.1016/j.polymer.2014.10.007 (2014).
Tsioris et al, "Fabrication of Silk Microneedles for Controlled-Release Drug Delivery", Advanced Functional Materials 22, 330-335, doi: 10.1002/adfm.201102012 (2012).
Tu et al, "Rapid prototyping of biodegradable microneedle arrays by integrating CO2 laser processing and polymer molding", Journal of Micromechanics and Microengineering, 26 (6) (2016).
Wallin et al, "A method to integrate patterned electrospun fibers with microfluidic systems to generate complex microenvironments for cell culture applications", Biomicrofluidics, 6 (2):24131 (2012).
Wang et al, "Electrospun nanofibrous membranes for highly sensitive optical sensors", Nano Letters 2 (11), 1273-1275 (2002).
Wang et al, "Recent advances in the design of polymeric microneedles for transdermal drug delivery and biosensing", Lab on a Chip (RSC Publishing) Issue 8 (2017).
Wermeling et al, "Microneedles permit transdermal delivery of a skin-impermeant medication to humans", Proceedings of the National Academy of Sciences of the United States of America 105, 2058-2063, doi:10.1073/pnas.0710355105 (2008).
Wu et al, "Template-assisted assembly of electrospun fibers", Polymer 51, 3244-3248, doi:10.1016/j.polymer. 04.039 (2010).
Yang et al, "A controlled biochemical release device with embedded nanofluidic channels", Applied Physics Letters, 100 (15) (2012).
Yang et al, "Electrospinning of nano/micro scale poly(L-lactic acid) aligned fibers and their potential in neural tissue engineering", Biomaterials, 26 (15), 2603-2610 (2005).
Yang et al, "Electrospun Nanofibrous Membranes: A Novel Solid Substrate for Microfluidic Immunoassays for HIV", Advanced Materials, 20 (24), 4770-75 (2008).
Yang et al, "From nano to micro to macro: Electrospun hierarchically structured polymeric fibers for biomedical applications", Progress in Polymer Science 81, 80-113 (2018).
Yang et al, "Promotion of skin regeneration in diabetic rats by electrospun core-sheath fibers loaded with basic fibroblast growth factor", Biomaterials, 32 (18), 4243-54 (2011).
Yoon et al, "Combinatorial Approach for Colorimetric Differentiation of Organic Solvents Based on Conjugated Polymer-Embedded Electrospun Fibers", Advanced Functional Materials, 19 (2), 209-214 (2009).
Yu et al, "Deformable mold based on-demand microchannel fabrication technology." Sensors and Actuators B—Chemical 2013, 183, 40-45 (2013).
Yu et al, "Patterned, highly stretchable and conductive nanofibrous PANI/PVDF strain sensors based on electrospinning and in situ polymerization", Nanoscale, 8 (5), 2944-50 (2016).

(56) References Cited

OTHER PUBLICATIONS

Zeng et al, "Biodegradable electrospun fibers for drug delivery", Journal of Controlled Release 92, 227-231, doi:10.1016/S0168-3659(03)00372-9 (2003).
Zhang et al, "Biomimetic and bioactive nanofibrous scaffolds from electrospun composite nanofibers", Int J Nanomedicine, 2 (4), 623-38 (2007).
Zhang et al, "Patterning of electrospun fibers using electroconductive templates", Advanced Materials 19:3664-67 (2007).
Zhao et al, "Nanofibrous Patterns by Direct Electrospinning of Nanofibers Onto Topographically Structured Non-Conductive Substrates", Nanoscale, 5(11):4993-5000 (2013).
Zhen et al, "Multifunctional liposomes constituting microneedles induced robust systemic and mucosal immunoresponses against the loaded antigens via oral mucosal vaccination". Vaccine 33, 4330-4340 (2015).
Zhu et al, "Electrospun fibrous mats with high porosity as potential scaffolds for skin tissue engineering", Biomacromolecules 9, 1795-1801, (2008).
Arya et al, "Microneedle patches for vaccination in developing countries", Journal of Controlled Release 240, 135-141, doi:10.1016/j.jconrel.2015.11.019 (2016).
Briggs et al, "Examining the formulation of emulsion electrospinning for improving the release of bioactive proteins from electrospun fibers", Journal of Biomedical Materials Research Part A, 102, 674 (2014).
Carlberg et al, Direct Photolithographic Patterning of Electrospun Films for Defined Nanofibrillar Microarchitectures Langmuir, 26 (4), 2235-2239 (2010).
Carson et al, "Tunable Release of Multiclass Anti-HIV Drugs that are Water-Soluble and Loaded at High Drug Content in Polyester Blended Electrospun Fibers", Pharmaceutical Research 33,125-136, doi:10.1007/s11095-015-1769-0 (2016).
Chakraborty et al, "Electrohydrodynamics: A facile technique to fabricate drug delivery systems", Advanced Drug Delivery Reviews 61, 1043-1054, doi:10.1016/j.addr.2009.07.013 (2009).
Cheng et al, "Engineering the Microstructure of Electrospun Fibrous Scaffolds by Microtopography", Biomacromolecules 14, 5, 1349-1360 doi:10.1021/bm302000n (2013).
Cho et al, "Replicable and Shape-Controllable Fabrication of Electrospun Fibrous Scaffolds for Tissue Engineering", Nanoscience and Nanotechnology 12, 9047-9050, doi:10.1166/jnn.2012.6758 (2012).
Cho et al, "Replicable multilayered nanofibrous patterns on a flexible film", Langmuir 26, 14395-14399, doi:10.1021/a102467u (2010).
Chou et al, "Current strategies for sustaining drug release from electrospun nanofibers", J Control Release 220, 584-591, doi:10.1016/j.jconrel.2015.09.008 (2015).
Chu et al, "Fabrication of Dissolving Polymer Microneedles for Controlled Drug Encapsulation and Delivery: Bubble and Pedestal Microneedle Designs", Journal of Pharmaceutical Sciences vol. 99, No. 10, 4228-4238 (2010).
Cormier et al, "Transdermal Delivery of Desmopressin Using a Coated Microneedle Array Patch System", J Control Release Jul. 7;97(3):503-11 (2004).
Creighton et al., "In situ integration of electrospun fibers with microneedles" draft manuscript for review (2019).
Creighton et al., "In situ 3D-patterning of electrospun fibers using two-layer composite materials" Sci Rep. 10:7949 (May 2020).
Davis et al, "Insertion of microneedles into skin: measurement and prediction of insertion force and needle fracture force", Journal of Biomechanics 37, 1155-1163, doi:10.1016/j.jbiomech.2003.12.010 (2004).
Deitzel et al, "Controlled deposition of electrospun poly(ethylene oxide) fibers", Polymer, 42 (19), 8163-8170 (2001).
Dempsey et al, "Micropatterning of Electrospun Polyurethane Fibers Through Control of Surface Topography", Macromolecular Materials and Engineering, 295 (11), 990-994 (2010).
Demuth et al, "Composite Dissolving Microneedles for Coordinated Control of Antigen and Adjuvant Delivery Kinetics in Transcutaneous Vaccination", Advanced Functional Materials 23, 161-172, (2013).
Demuth et al, "Implantable silk composite microneedles for programmable vaccine release kinetics and enhanced immunogenicity in transcutaneous immunization", Adv Healthc Mater. Jan; 3(1): 47-58 (2014).
Ding et al, "Selective Nanofiber Deposition through Field-Enhanced Electrospinning", Langmuir 25, 9648-9652, doi:10.1021/la901924z (2009).
Dong et al, "Degradation of electrospun nanofiber scaffold by short wave length ultraviolet radiation treatment and its potential applications in tissue engineering", Tissue Engineering Part A 2008, 14 (8), 1321-1329 (2008).
Donnelly et al, "Design, Optimization and Characterisation of Polymeric Microneedle Arrays Prepared by a Novel Laser-Based Micromoulding Technique", Pharmaceutical Research 28, 41-57, doi:10.1007/s11095-010-0169-8 (2011).
Frizzel et al, "Protein-loaded emulsion electrospun fibers optimized for bioactivity retention and pH-controlled release for peroral delivery of biologic therapeutics", International Journal of Pharmaceutics 533, 99-110, doi:10.1016/j.jpharm.2017.09.043 (2017).
Fukushima et al, "Two-Layered Dissolving Microneedles for Percutaneous Delivery of Peptide/Protein Drugs in Rats", Pharmaceutical Research 28/1 7-21 (2010).
Gibson et al, "Transport properties of porous membranes based on electrospun nanofibers", Colloids and Surfaces a—Physicochemical and Engineering Aspects, 187, 469-481 (2001).
Gill et al, "Effect of microneedle design on pain in human subjects", Clin J Pain 24, 585-594 (2008).
Goktas et al, "Biomechanical behavior of oral soft tissues", J Periodontol, 82 (8), 1178-86 (2011).
Gonzalez-Vazquez et al, "Transdermal delivery of gentamicin using dissolving microneedle arrays for potential treatment of neonatal sepsis", Journal of Controlled Release 265, 30-40, doi:10.1016/j.jconrel.2017.07.032 (2017).
Goonoo et al, "Drug Loading and Release from Electrospun Biodegradable Nanofibers", Journal of Biomedical Nanotechnology, 10, 9, 2173-2199(27) (2014).
Gopal et al, "Electrospun nanofibrous filtration membrane", Journal of Membrane Science, 281 (1-2), 581-586 (2006).
Goyal et al, ""Nanoparticles and Nanofibers for Topical Drug Delivery", Journal of Controlled Release vol. 240, 28 77-92 (2016)".
Guex et al, Anisotropically oriented electrospun matrices with an imprinted periodic micropattern: a new scaffold for engineered muscle constructs. Biomedical Materials 8, doi:10.1088/1748-6041/8/2/021001 (2013).
Ito et al, "Self-dissolving Microneedles for the Percutaneous Absorption of EPO in Mice", J Drug Target 14(5):255-61 (2006).
Ji et al, "Fibrous Scaffolds Loaded With Protein Prepared by Blend or Coaxial Electrospinning", Acta Biomaterialia, 6 (11):4199-207 (2010).
Kim et al, "Hydrogel swelling as a trigger to release biodegradable polymer microneedles in skin", Biomaterials 33, 668-678, doi:10.1016/j.biomaterials.2011.09.074 (2012).
Kim et al, "Microneedles for drug and vaccine delivery", Adv Drug Deliv Rev 64, 1547-1568, doi:10.1016/j.addr.2012.04.005 (2012).
Lahiji et al, "A patchless dissolving microneedle delivery system enabling rapid and efficient transdermal drug delivery", Scientific Reports 5:7914-7920 (2015).
Lavielle et al, "Structuring and Molding of Electrospun Nanofibers: Effect of Electrical and Topographical Local Properties of Micro-Patterned Collectors", Macromolecular Materials and Engineering 297, 958-968, doi:10.1002/mame.201100327 (2012).
Lee et al, "Dissolving Microneedle Patch for Transdermal Delivery of Human Growth Hormone", Small 7, 531-539, doi:10.1002/smll.201001091 (2011).
Lee et al, "Dissolving microneedles for transdermal drug delivery", Biomaterials 29, 2113-2124, doi:10.1016/j.Biomaterials12.048 (2008).
Lee et al. "Femtosecond laser ablation enhances cell infiltration into three-dimensional electrospun scaffolds", Acta Biomater 8, 2648-2658, doi:10.1016/j.actbio.2012.04.023 (2012).

(56) References Cited

OTHER PUBLICATIONS

Lee et al. "Polymeric nanofiber web-based artificial renal microfluidic chip", Biomedical Microdevices, 9 (4), 435-442 (2007).

Leung et al,"Effect of face velocity, nanofiber packing density and thickness on filtration performance of filters with nanofibers coated on a substrale", Separation and Purification Technology, 71 (1), 30-37 (2010).

Li et al, "Electrospun nanofibrous structure: A novel scaffold for tissue engineering", Journal of Biomedical Materials Research 60, 613-621, (2002).

Li et al, Collecting electrospun nanofibers with patterned electrodes. Nano Letters 5, 913-916, (2005).

Lim et al, "Micropatterning and Characterization of Electrospun Poly(epsilon-Caprolactone)/Gelatin Nanofiber Tissue Scaffolds by Femtosecond Laser Ablation for Tissue Engineering Applications", Biotechnology and Bioengineering, 108 (1), 116-126 (2011).

Liu et al, "Electrospun Fibrous Mats on Lithographically Micropatterned Collectors to Control Cellular Behaviors", Langmuir 28, 17134-17142, doi:10.1021/la303490x (2012).

Liu et al, "Fabrication of composite microneedles integrated with insulin-loaded $CaCO_3$ microparticles and PVP for transdermal delivery in diabetic rats", Materials Science and Engineering: 90:180-188 (2018).

Liu et al, "Piezoelectric properties of PVDF/MWCNT nanofiber using near-field electrospinning", Sensors and Actuators a-Physical, 193, 13-24 (2013).

Luu et al, "Development of a nanostructured DNA delivery scaffold via electrospinning of PLGA and PLA-PEG block copolymers", J Control Release, 89 (2), 341-53 (2003).

Moga et al, "Rapidly-dissolvable Microneedle Patches via a Highly Scalable and Reproducible Soft Lithography Approach", Adv Mater 25(36): 5060-5066 (2013).

\* cited by examiner

INTEGRATED FIBER MICRONEEDLE DEVICE FOR DRUG AND VACCINE DELIVERY

CROSS-REFERENCE TO RELATED APPLICATION

This application claims priority to U.S. Provisional Patent Application No. 62/719,812, filed Aug. 20, 2018, which is incorporated herein by reference.

STATEMENT REGARDING FEDERAL FUNDING

This invention was made with government support under HD075703, awarded by the National Institutes of Health. The government has certain rights to the invention.

BACKGROUND

Microneedle arrays are a method for delivering DNA, vaccines, drugs, or other substances into a body through the skin. Microneedle arrays generally include a plurality of microneedles attached to a planar backing. Each microneedle may contain an amount of a drug, small molecule, biologic, vaccine, DNA, or other substance that can be delivered from the microneedle into tissue when the microneedle has penetrated the tissue. Additionally or alternatively, microneedles can be configured to facilitate tissue ingrowth into the microneedles (e.g., by including materials that dissolve after insertion to provide cavities into which cells or tissue can grow). Microneedle arrays may be used as an alternative to hypodermic needles to deliver biologically active substances and can be tailored to provide a controlled release profile.

SUMMARY

It is beneficial to create microneedle arrays wherein fibers (e.g., drug-bearing fibers) are preferentially disposed within the microneedles (e.g., the tips and/or distal portions of the microneedles) relative to the backing of the microneedle array and/or proximal portions of the microneedles. Such a preferential allocation of the fibers can provide a variety of benefits. By locating more of the fibers within the microneedles and/or the tips of the microneedles, a greater proportion of the fiber material is able to release drugs or other substances into skin. This can allow for more controlled drug release and reduced cost, especially where the substance released is a biologic or other expensive substance. Additionally, the presence of electrospun fibers within a microneedle can act to increase the strength of the microneedle, facilitating penetration of skin. The properties of the fibers and the bulk material that the fibers are embedded within can be controlled to adjust a release profile of a drug or other substance from the microneedles.

However, it can be difficult to achieve such preferential disposition of fibers in the microneedles of a microneedle array. For example, electrospinning the fibers onto a wholly conductive mold (that includes negative features for the microneedles to be formed) can result in a large amount of the fibers being deposited in the backing of the array, rather than in the microneedles. This can result in less drug being delivered, increased cost due to wasting of the drug that is embedded in the backing of the array rather than in the microneedles, or other unwanted effects.

To address these issues and to increase the proportion of the fibers that are disposed within the microneedles of the microneedle array relative to the backing of the microneedle array, a surface layer of the mold used to form the microneedle array can be made insulating or otherwise less conductive than an underlying layer of the mold (e.g., than a bulk material of the mold). By providing a surface layer that is insulating, the electrical field around the mold during electrospinning can be modified such that electrospun fibers are preferentially depositing within the negative features of the mold (e.g., in regions that will become the tips of the microneedles) relative to being deposited on the surface of the mold. Once the fibers are electrospun and deposited into the negative features of the mold, a solution can be deposited onto the mold and cured (e.g., by drying, exposure to a chemical agent, exposure to UV light) to form the microneedle array.

Such a mold could be formed by creating a mold having two discrete layers (e.g., a first insulating layer formed atop a conductive layer). Alternatively, such a mold could be formed from a single continuous piece of material that exhibits a gradient of conductivity or some other depth-dependent conductivity throughout the piece of material (e.g., a depth-dependent distribution of carbon black or of some other conductive particles within the piece of material).

An aspect of the present disclosure relates to a method for forming a microneedle array, the method including: (i) depositing, by electrospinning, a plurality of fibers onto a first surface of a mold; (ii) depositing a precursor material onto the first surface of the mold; and (iii) curing the precursor material such that the precursor material forms a microneedle array with the deposited plurality of fibers. The mold includes a first layer that is nonconductive and a second layer that is conductive, and the first layer is disposed between the second layer and the first surface such that the plurality of fibers are preferentially deposited into the negative features. The formed microneedle array includes (a) a plurality of microneedles containing respective portions of the plurality of fibers, and (b) a backing to which each microneedle of the plurality of microneedles is coupled. The mold includes a plurality of negative features formed therein from the first surface.

Another aspect of the present disclosure relates to a microneedle array including: (i) a plurality of microneedles; (ii) a backing to which each microneedle of the plurality of microneedles is coupled; and (iii) a plurality of fibers, wherein the plurality of fibers are preferentially disposed within the plurality of microneedles relative to the backing.

Yet another aspect of the present disclosure relates to a mold having a first surface, the mold including: (i) a first layer that is nonconductive; and (ii) a second layer that is conductive. A plurality of negative features penetrate fully through the first layer. The negative features correspond to a plurality of microneedles.

These as well as other aspects, advantages, and alternatives will become apparent to those of ordinary skill in the art by reading the following detailed description with reference where appropriate to the accompanying drawings. Further, it should be understood that the description provided in this summary section and elsewhere in this document is intended to illustrate the claimed subject matter by way of example and not by way of limitation.

Figure 1:
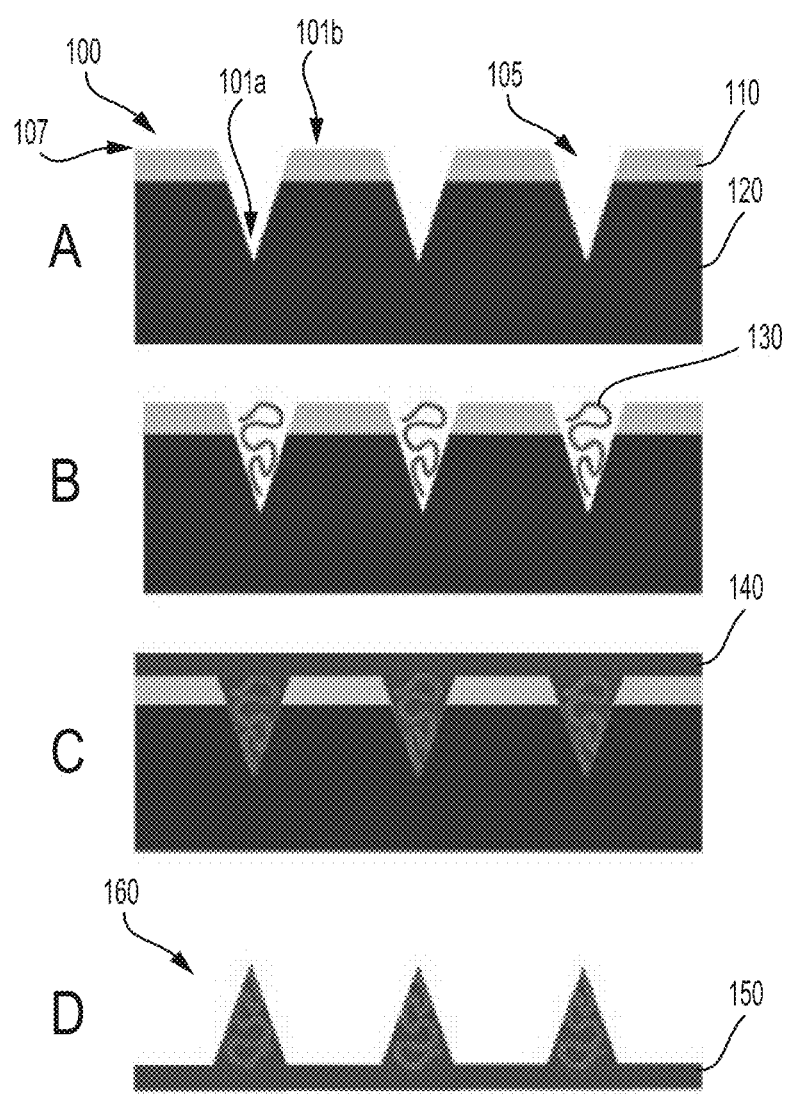
FIG. 1 depicts an example method for forming a microneedle array.

The patent or application file contains at least one drawing executed in color. Copies of this patent or patent application publication with color drawing(s) will be provided by the Office upon request and payment of the necessary fee.

DETAILED DESCRIPTION

Examples of methods and systems are described herein. It should be understood that the words "exemplary," "example," and "illustrative," are used herein to mean "serving as an example, instance, or illustration." Any embodiment or feature described herein as "exemplary," "example," or "illustrative," is not necessarily to be construed as preferred or advantageous over other embodiments or features. Further, the exemplary embodiments described herein are not meant to be limiting. It will be readily understood that certain aspects of the disclosed systems and methods can be arranged and combined in a wide variety of different configurations.

I. Overview

Microneedle arrays are a method for delivering drugs, vaccines, DNA, biologics, small molecules, or other substances into the skin. Microneedle arrays can be easier to apply than alternatives like hypodermic needles, allowing for self-administration. Additionally, microneedle arrays can be administered with less pain and/or without triggering needle phobias or other negative psychological effects. Further, since the microneedle array can be left on the skin for protracted period of time (e.g., adhered to the skin following initial application), microneedle arrays can provide extended, controlled release of drugs or other substances.

It is desirable to fabricate microneedle arrays having embedded within the microneedles a plurality of fibers (e.g., electrospun fibers) that may contain or transmit drugs or other substances. The embedding of such fibers within the microneedles can provide a variety of benefits, including providing greater control of the release of drugs or other substances from the fibers and/or from a bulk material of the microneedles, stabilizing biologics or other sensitive compounds within the fibers, improving control of drug dosing and reducing cost by ensuring that drug contained within the fibers is deposited entirely or predominantly within the microneedles such that all or the majority of the drug is delivered into skin, increasing the mechanical strength of the microneedles, or other benefits.

However, it can be difficult to ensure that the fibers are preferentially disposed within the microneedles (e.g., near distal tips of the microneedles) instead of within a backing of the array and/or proximal portions of the microneedles (e.g., near the base of the needles, where drugs or other substances are less likely to be delivered into skin). For example, electrospinning fibers toward a conventional conductive mold (e.g., a mold composed of metal or other conductive materials and that includes negative features in which the microneedles can be formed) by applying a high voltage between the mold and a syringe depositing fiber precursor material can result in the fibers being deposited mostly on the surface of the mold, rather than within the negative features. As a result, microneedle arrays formed in the manner will have most of the deposited fibers embedded within the backing of the array rather than in the microneedles (see, e.g., frames 'a' and 'b' of FIG. 10). The fibers deposited on the surface can be ablated (e.g., using a laser), but this does nothing to increase the amount of the fibers that is disposed within the microneedles. Both methods result in the waste of any drug or other beneficial substance in the fibers that are deposited on the surface.

The amount and/or proportion of electrospun fibers that are deposited within the negative features of the mold (and thus that will be embedded within the microneedles formed in the negative features), the mold can be formed to have a surface layer that is non-conductive or otherwise less conductive than an underlying layer of the mold. This non-conductive layer can change the electrical field around the mold during electrospinning such that fibers emitted from the syringe are preferentially deposited within the negative features of the mold. For example, more than 75%, more than 90%, more than 95%, or more than 99% of the deposited fibers could be deposited within the negative features of the mold.

A cross-sectional view of such a mold is depicted in frame 'a' of FIG. 1. The mold 100 includes a first layer 110 disposed on a second layer 120. The mold 100 has a first surface 107 that is directed toward the source of electrospun fibers during fiber deposition. The first layer 110 is disposed between the second layer 120 and the surface 107. A plurality of negative features 105 are formed into the mold from the surface 107. The negative features 105 are shaped to correspond to the desired shape of the microneedles (e.g., wedge-shaped, conical, pyramidal). The second layer 120 is conductive (e.g., composed of a conductive metal, of a conductive polymer, of a polymer impregnated with conductive particles) and the first layer 110 is non-conductive (e.g., insulating) or otherwise less conductive than the second layer 120.

The relative conductivities and dimensions of the first 110 and second 120 layers and the negative features 105 can be selected to result (as shown in frame 'b' of FIG. 1) in the preferential deposition of electrospun fibers 130 within the negative features 105. This can include changing the electrical field such that an electrical field strength within the negative feature 105 (e.g., at a base of the negative feature 101a, where the tip of the microneedle will be formed) is greater than an electrical field strength at the surface of the mold (e.g., at a point 101b on the surface where there is not a negative feature).

Figure 9:
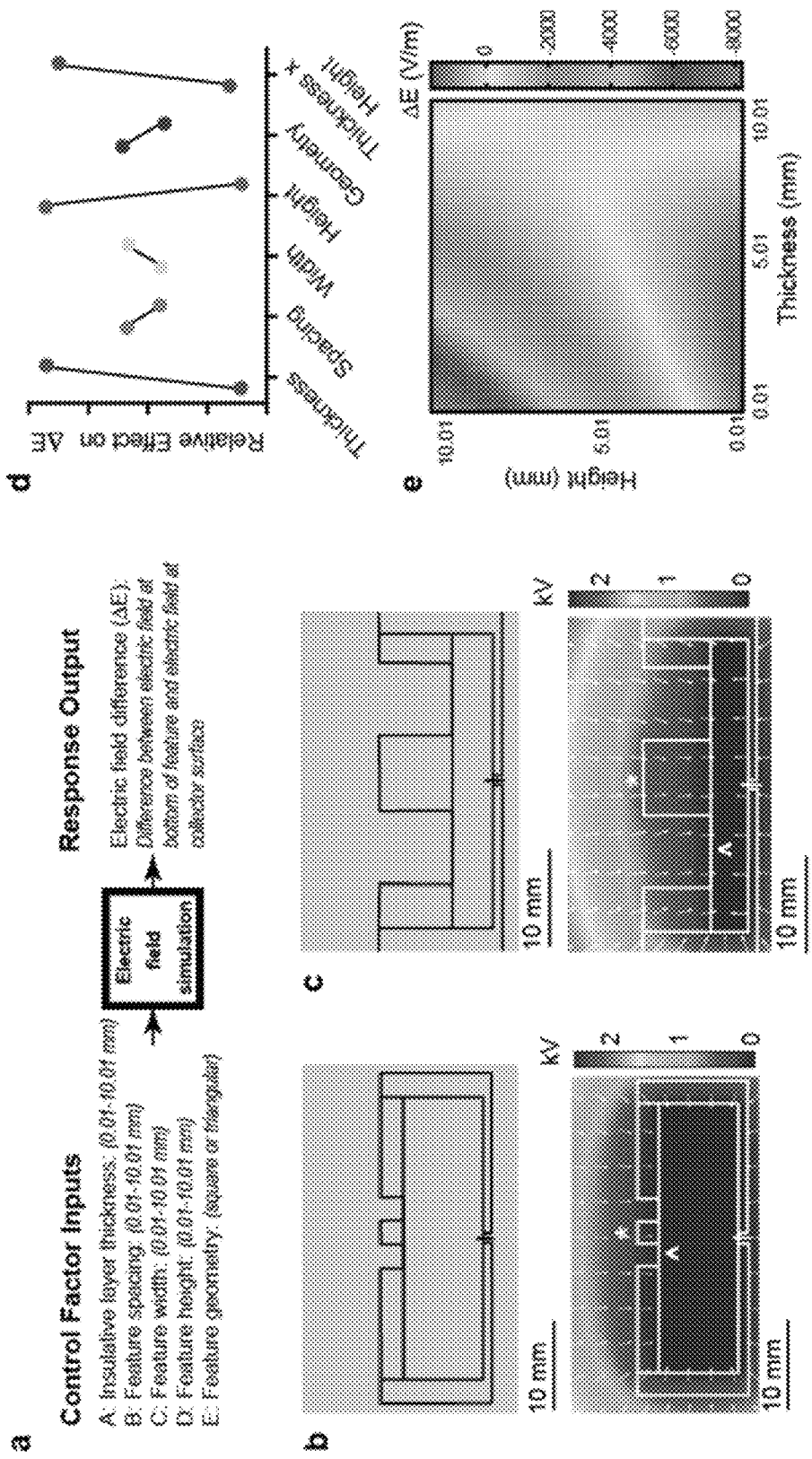
FIG. 9 illustrates simulation results related to fiber deposition across a range of needle and mold dimensions and fiber compositions.

A depth of the negative features 105 could be controlled, relative to the thickness of the non-conductive layer 110, to control where within the negative feature 105 the fibers are preferentially deposited. In some embodiments, the depth of the features 105 could be greater than the thickness of the non-conductive layer 110 such that the negative features penetrate all the way through the non-conductive first layer 110 and the electrospun fibers are attracted to the electrical potential of the conductive second layer 120. For example, the thickness of the first layer 110 could be greater than 350 microns, and the negative features 105 could have depths of 400 microns, 450 microns, 500 microns, or some other depth greater than 350 microns. Accordingly, in order to preferentially deposit the fibers at depths along the microneedles such that the fibers are likely to release drug into the skin, the thickness of the non-conductive first layer 110 could be greater than an expected thickness of a human or animal stratum corneum, e.g., greater than such an expected thickness by a safety margin. The thickness of the non-conductive first layer 110 could be some greater thickness in order to target deeper structures within skin. Frame 'e' of FIG. 9 shows the relationship between the depth of the negative features, the thickness of the first layer, and the preferential deposition of fibers within the negative features relative to other regions of the mold.

Note that, while FIG. 1 illustrates the first 110 and second 120 layers as being wholly discrete layers of separate materials (e.g., separately formed layers of separate materials), the conductive and non-conductive layers of a mold as described herein may be layers of a single continuous piece of material. The difference in conductivity between conductive and non-conductive layers of such a single piece of material could be achieved via a variety of methods. For example, a rate of a temperature gradient or some other gradient could be applied to the material of the mold during formation to result in location-dependent conductivity within the material. In another example, the distribution of conductive particles (e.g., particles of a metal, particles of carbon black) within the material could be controlled (e.g., by centrifuging, by applying a magnetic field to magnetic conductive particles) to result in location-dependent conductivity within the material. In another example, light (e.g., ultraviolet light), an ion beam, or some other directed energy could be applied to the formed material in order to selectively change the conductivity of the material in a location-dependent manner. For example, the material could be a conductive polymer (e.g., PEDOT), and ultraviolet light or some other energy could be applied to one surface of the material in order to break the polymer backbone, to activate a chemical substance embedded within the material, or to result in some other process that causes a reduction in conductivity of the material, resulting in location-dependent conductivity within the material. In yet another example, the precursor solution could be cured as it is deposited, allowing the conductivity of the mold thus formed to vary across depth by varying the composition of the precursor solution as it is applied (e.g., to change an amount of a conductive polymer monomer unit or an amount of conductive particles in the solution).

Once the fibers 130 have been deposited onto the mold 100 (e.g., within the negative features 105 of the mold), a precursor solution 140 can be deposited onto the surface of the mold. This is shown in frame 'c' of FIG. 1. The precursor solution 140 could be a solution of one or more varieties of monomer units, solvents, polymerization initiators, cross-linking promoters, softening or stiffening agents, stabilizers, DNA, RNA, small molecules, liposomes, drugs or other substances that can be released from the bulk of the microneedles once the precursor solution 140 is cured, or some other substances according to an application. The precursor solution 140 fills the negative features and coats the surface 107 of the mold such that the precursor solution 140 can be cured to form a microneedle array 160. The precursor solution 140 could be centrifuged subsequent to being applied to the mold 100 in order to ensure that it backfills the negative features 105.

The microneedle array 160 formed via this process is shown in frame 'd' of FIG. 1. Curing the precursor solution 140 results in the precursor solution 140 forming a backing 150 and the bulk of a plurality of microneedles in which are embedded respective portions of the plurality of fibers 130. The formed microneedles are thus mechanically coupled to the backing, allowing the backing to be used to apply the plurality of microneedles to skin or other tissue (e.g., buccal tissue, some other mucosa or other tissue of some other external body surface, the tissue of an internal organ) and to remove the microneedles from the skin or other tissue after the microneedle array has been applied to the skin or other tissue.

A small molecule, a biologic, an antibody, RNA, DNA, or some other pharmaceutically active substance could be disposed within one or both of the fibers or the bulk material (i.e., the material formed from the deposited precursor solution) of the microneedle array. The fibers could include polyvinyl alcohol (PVA), polycaprolactone (PCL), poly(lactic-co-glycolic acid) (PLGA), or some other material suitable for electrospinning, dissolving in bodily tissues, and/or for drug release. The bulk material could include poly (acrylic acid) (PAA) or some other material suitable for backfilling, curing, providing mechanical strength, dissolving in bodily tissue, and/or for drug release (from the bulk material and/or from drug-bearing fibers embedded therein). The fiber composition, bulk material composition, and/or microneedle geometry could be chosen such that the microneedles are capable of penetrating skin, e.g., capable of penetrating human or animal stratum corneum. For example, the microneedles could exhibit a failure force, in response to lengthwise compression, greater than 0.04 newtons per microneedle.

The mold could be composed of a variety of conductive and non-conductive or otherwise less-conductive materials. Conductive materials could include conductive metals, conductive semiconductors (e.g., doped semiconductors), conductive polymers (e.g., PEDOT), non-conductive materials (e.g., polydimethylsiloxane (PDMS)) impregnated with particles of a conductive material (e.g., particles of gold, silver, or some other conductive metal, particles of carbon black), or some other conductive material. For example, the conductive layer of a mold could be composed of PDMS containing 7.5% particles of carbon black by weight. Non-conductive materials could include non-conductive metals, non-conductive semiconductors, non-conductive polymers, or some other non-conductive material. Note that a "non-conductive" layer, or "non-conductive" material, as used herein, my refer to insulating materials or may refer to materials that are conductive, but that are less conductive than some other material. So, for example, a surface layer of a mold could be composed of a "non-conductive" material that has a non-zero conductivity that is less than the conductivity of an underlying layer of "conductive" material. Such "less conductive" non-conductive materials could be chosen in order to control a degree to which electrospun fibers are preferentially deposited within negative features of a mold, e.g., in order to deposit a specified non-zero amount of fibers on the surface of the mold.

A mold as described herein could be formed in a variety of ways. The mold could, itself, be formed in a master mold such that the formed mold has the plurality of negative features. Additionally or alternatively, the layers of conductive and non-conductive material could be formed and subsequently the negative features could be formed via subtractive processes, e.g., by using a drill, a laser, or some other means to remove material to form the negative features.

Figure 2:
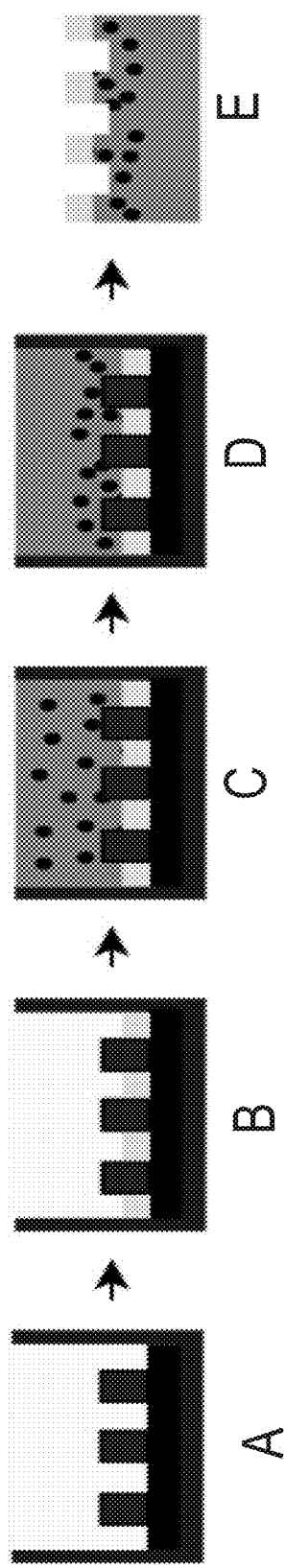
FIG. 2 depicts an example method for forming a mold.

FIG. 2 shows steps in a process of making a mold using a master mold. Frame 'a' shows the master mold empty, having a number of positive features that correspond to the negative features of the mold to be formed. Frame 'b' shows a first precursor material deposited into the master mold; this first precursor material is cured (e.g., by drying, exposure to UV light, allowing an internal reaction of the material to proceed for a specified period of time) to form the first, non-conductive layer of the mold.

Frame 'c' of FIG. 2 shows a second precursor materal having been added to the master mold. The second precursor material of FIG. 2 includes a plurality of conductive particles (e.g., carbon black). In order to increase the conductivity of the second layer while reducing the amount of such conductive particles in the second precursor material (e.g., to reduce an effect on the viscosity of the second precursor material caused by higher amounts of the particles), the second precursor material could be centrifuged after being deposited on the master mold and before being cured. A second, conductive layer resulting from such centrifugation and curing is shown in frame 'd' of FIG. 2. The completed mold, having been released from the master mold, is shown in frame e' of FIG. 2.

Note that the 'centrifuging' step between frames 'c' and 'd' of FIG. 2 may be omitted where not needed. For example, in embodiments wherein the second precursor material forms a layer that is intrinsically conductive (e.g., PEDOT) or where the distribution of conductive particles prior to centrifugation is acceptable. Centrifugation may additionally or alternatively be applied to impose a specified pattern (e.g., gradient) in the conductivity of the formed materials/mold as a function of depth. This could be done, e.g., to result in a surface layer that is less conductive than an underlying bulk layer, such that the mold can be formed from a single continuous piece of material instead of multiple separately formed layers.

Figure 3:
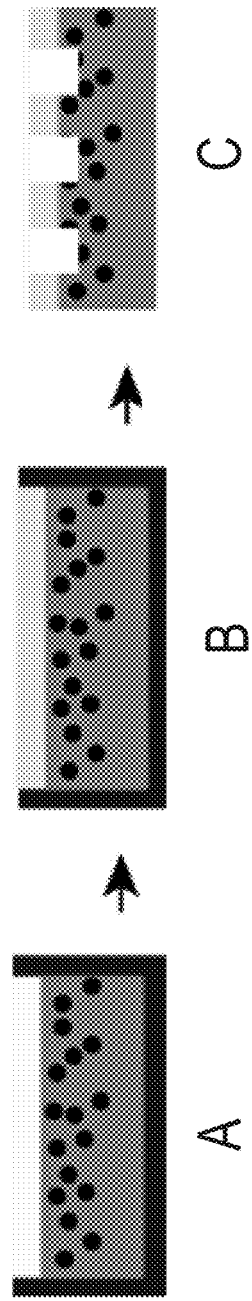
FIG. 3 depicts an example method for forming a mold.

A mold as described herein could additional or alternatively be formed via subtractive processes. Frame 'a' of FIG. 3 shows a conductive layer (e.g., a layer of material containing a plurality of conductive particles) formed in a master mold. Forming such a layer could include depositing a precursor material into the mold, centrifuging the precursor material, curing the precursor material, and/or other processes. A second, non-conductive layer is formed on the conductive layer (shown in frame 'b'). A plurality of negative features (corresponding to microneedles of a microneedle array to be formed using the formed mold) are then formed in the multi-layer structure via subtractive processes (e.g., laser ablation, mechanical drilling), as shown in frame 'c' of FIG. 3.

II. Example Methods

Figure 4:
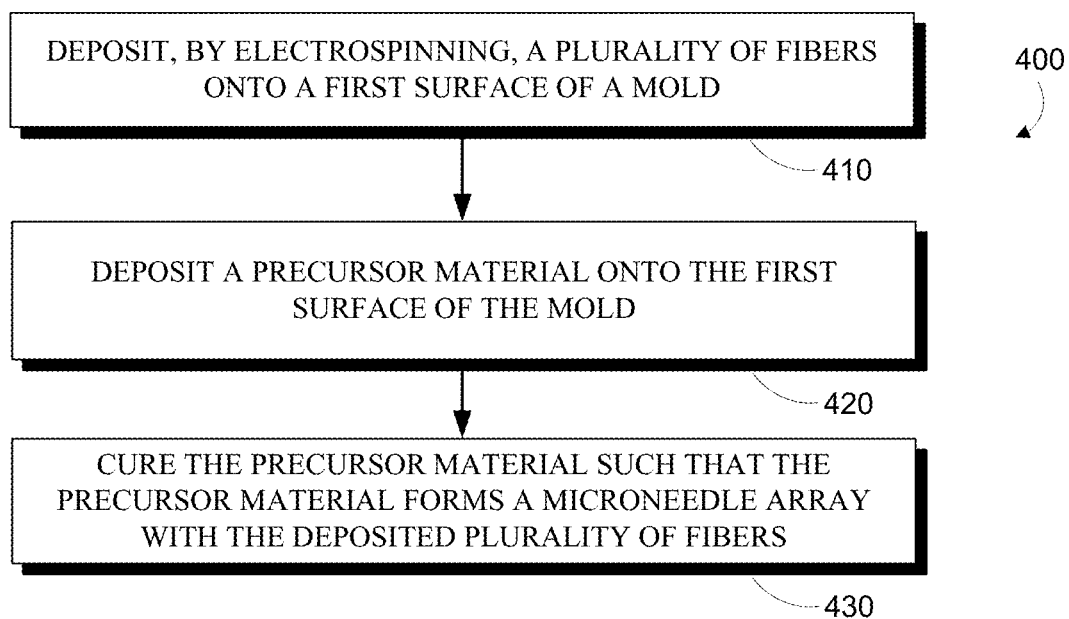
FIG. 4 is a flowchart of an example method.

FIG. 4 is a flowchart of a method 400 for forming a microneedle array. The method 400 includes depositing, by electrospinning, a plurality of fibers onto a first surface of a mold (410). A plurality of negative features are formed into the mold from the first surface. The mold includes a first layer that is nonconductive and a second layer that is conductive, and wherein the first layer is disposed between the second layer and the first surface such that the plurality of fibers are preferentially deposited into the negative features.

The method 400 additionally includes depositing a precursor material onto the first surface of the mold (420). The method 400 further includes curing the precursor material such that the precursor material forms a microneedle array with the deposited plurality of fibers (430). The formed microneedle array includes (i) a plurality of microneedles containing respective portions of the plurality of fibers, and (ii) a backing to which each microneedle of the plurality of microneedles is coupled.

Figure 5:
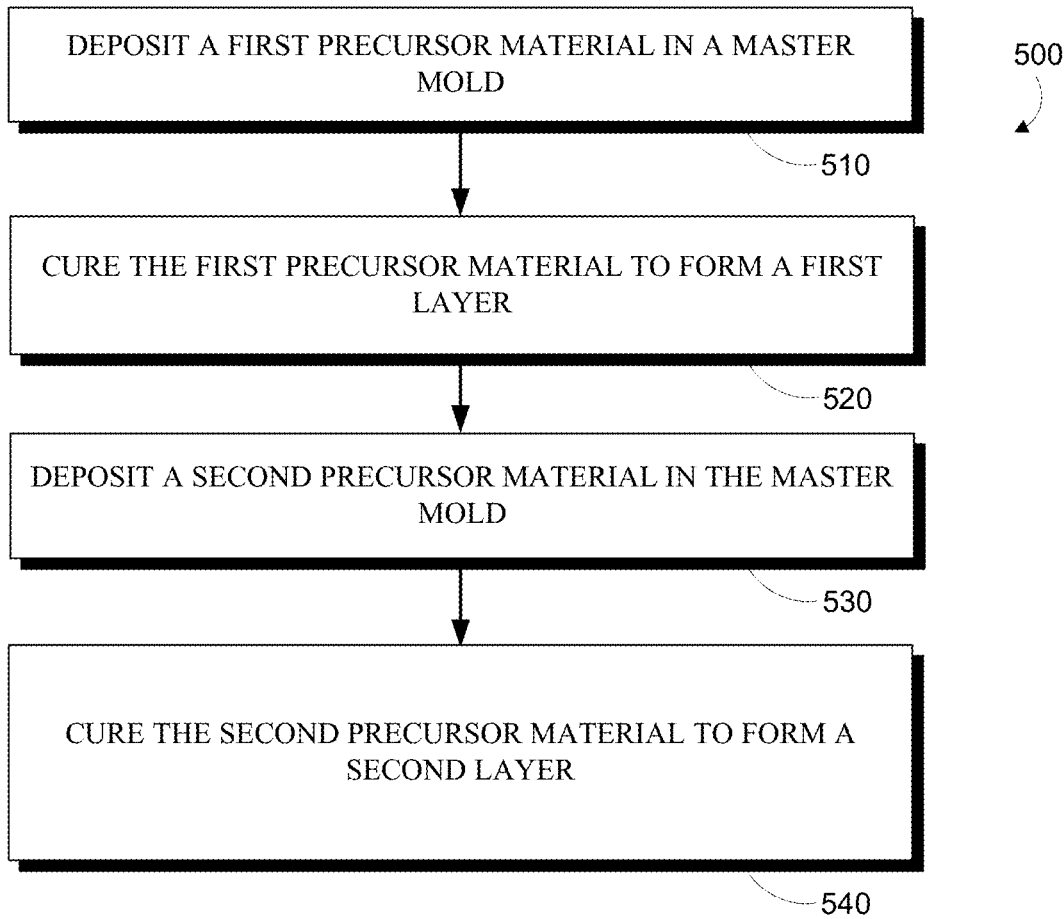
FIG. 5 is a flowchart of an example method.
Figure 6:
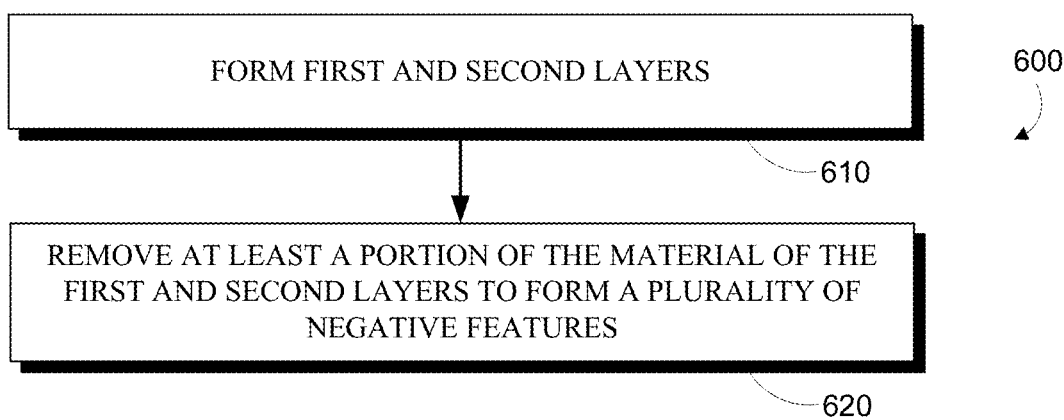
FIG. 6 is a flowchart of an example method.

FIG. 5 is a flowchart of a method 500 for forming a mold that may be used to form a microneedle array according to the method 400 of FIG. 4. Such a mold includes a first layer that is nonconductive and a second layer that is conductive. Such a mold additionally includes a plurality of negative features that are formed into the mold from a first surface of the mold; the first layer is disposed between the second layer and the first surface. The method 500 includes depositing a first precursor material in a master mold (510). The master mold includes a plurality of positive features corresponding to the negative features of the mold to be formed by the method 500. The method 500 additionally includes curing the first precursor material to form the first layer of the mold to be formed by the method 500 (520). The method 500 additionally includes depositing a second precursor material in the master mold (530). The method 500 additionally includes curing the second precursor material to form the second layer of the mold to be formed by the method 500 (540). 100471 FIG. 6 is a flowchart of a method 600 for forming a mold that may be used to form a microneedle array according to the method 400 of FIG. 4. Such a mold includes a first layer that is nonconductive and a second layer that is conductive. Such a mold additionally includes a plurality of negative features that are formed into the mold from a first surface of the mold; the first layer is disposed between the second layer and the first surface. The method 600 includes forming the first and second layers of the mold to be formed by the method 600 (610). The method 600 additionally includes curing the first precursor material to form the first layer of the mold to be formed by the method 500 (520). The method 500 additionally includes removing at least a portion of the material of the first and second layers to form the plurality of negative features of the mold to be formed by the method 500 (520).

The methods above 400, 500, 600 could include additional elements or features.

III. Experimental Results

A delivery platform was investigated that preferentially incorporates electrospun fibers into microneedles relative to an array backing to which the microneedles are attached. Electrospun fibers integrated into microneedle arrays can collectively improve microneedle capabilities including efficient loading, tunable release kinetics, and the ability to stabilize sensitive biologics. Integration was achieved in situ by collecting electrospun fibers on conductive microneedle molds. Fiber integration properties such as fiber selectivity for the microneedle cavities and the fiber location within the cavities was controlled and optimized by tailoring features of the microneedle mold design and the electrospinning solution properties. This in situ strategy translates to various fiber materials and to a range of relevant microneedle dimensions. Integrated fiber microneedles can achieve relevant drug loading and release properties, and they possess sufficient mechanical strength to puncture tissue.

A robust and reproducible method was developed for in situ electrospinning of polymeric fibers into microneedle cavities using negative micropatterned molds. Electrospun fibers were incorporated into dissolving microneedles at high yield and selectivity for the microneedles compared to the backing support. This integrated fiber microneedle system is broadly tunable, with demonstrated compatibility with different microneedle geometries, fiber materials, and microneedle spacing. Integrated fiber microneedles are mechanically strong, with compression forces meeting literature targets and demonstrated puncture of non-human primate dermal and buccal tissue. This device could be used in future studies to deliver a broad range of biologics with tunable release kinetics to a variety of tissues.

Example devices, methods, and systems are described herein. It should be understood the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood other embodiments may include more or less of each element shown in a given Figure. Further, some of the illustrated elements may be combined or omitted. Yet further, an example embodiment may include elements not illustrated in the Figures. As used herein, with respect to measurements, "about" means+/−5%.

Electrospun fibers were integrated with microneedles using an in situ approach. Microneedle molds with differential surface conductivity were designed to modulate the local electric field and achieve preferential fiber deposition in the microneedle cavities. This generalizable strategy combines the broad drug delivery capabilities of electrospun fibers with the direct tissue access capabilities of microneedles.

Microneedle technology is an effective mode of transdermal drug and vaccine delivery, and is an alternative to hypodermic needle injections. Microneedles are able to disrupt the stratum corneum, the main physical barrier to transdermal delivery of biologics, and they can achieve both local and systemic delivery. Microneedles also offer practical advantages over hypodermic needles such as minimal pain and potential for self-administration. Dissolvable microneedles also eliminate the need to safely dispose of biohazardous sharps waste, making them an attractive delivery system for low-resource settings.

Sustained release can be achieved in dissolving microneedle devices through incorporation of materials like crosslinked silk into the microneedles. Release can also be sustained by incorporating PLGA nanoparticles into the microneedles or by formulating the entire needle as a PLGA depot. Additionally, cell targeting can be achieved through inclusion of liposomes conjugated with molecules to facilitate cell-specific uptake. The breadth of control over local drug release can be expanded using the methods and systems described herein, and additional strategies to decouple microneedle mechanical properties from the type and quantity of drug loaded can enable further application of microneedles for existing and emerging biomedical challenges.

Electrospun fibers have unique properties as a drug and vaccine delivery platform that can provide additional functionality to microneedle devices. Electrospun polymeric fibers are capable of incorporating a broad range of biologics, including small molecules, proteins, and DNA. They also have a high loading capacity and loading efficiency, meaning that fibers may enable transdermal delivery of low potency biologics and maximize encapsulation of expensive biologics. Electrospun fibers can be fabricated out of a wide range of materials that enable precise control over release kinetics. Finally, electrospun polymeric fibers have a high surface area to volume ratio providing opportunities for cell-material interactions. Therefore, integrating electrospun fibers with microneedles can provide a single fabrication strategy to generate microneedles with broad functionality.

In at least one embodiment, to take full advantage of the drug delivery capabilities of electrospun fibers, the fibers were incorporated into the needles, but not the backing support, of the completed microneedle device. This approach improves delivery efficiency by ensuring that the fibers are delivered into the tissue rather than remaining on the tissue surface. Additionally, by incorporating fibers into only the needles, the fibers can be implanted into the tissue to release their cargo over extended periods of time.

Several attributes are advantageous for an in situ integration strategy to incorporate electrospun fibers into the cavities of a microneedle mold. First, in situ integration has potential to minimize reagent waste compared to processes in which fibers are applied to the entire mold and then selectively removed from the mold surface. Nanoparticle or liposome formulations can be incorporated using this strategy, and they can be successfully recovered after removal from the mold. However, electrospun fibers that have been formed into a connected mat structure are more difficult to recover and reuse excess fibers from. Next, in situ integration is potentially more reproducible than integration by mechanical packing processes because it is dependent on controllable material properties and design rather than user expertise. Finally, highly porous fiber architectures can be achieved by electrospinning onto micropatterned substrates. This porous architecture may improve cell infiltration into the implanted fiber scaffold and therefore take full advantage of the high surface area to volume ratio of electrospun fibers. Integration strategies incorporating a pre-fabricated mat of electrospun fibers do not exhibit this increased porosity and require additional processing to allow cell infiltration.

Fibers were integrated into microneedle cavities with relevant geometry to enable tissue puncture. Fibers can be electrospun onto substrates with pyramidal cavities with an aspect ratio of 1:1, but this aspect ratio is not sufficient for microneedles to easily puncture tissue. Fibers were preferentially deposited within the microneedle cavities relative to fiber deposition on the mold surface. This is a design constraint unique to integrated fiber microneedles. Electrospun fibers can be isolated onto the tips of positive pyramidal structures based on enhancement of electric field forces at the tips of the structures. However, fiber isolation in negative features is difficult because the electric field forces are likely to be larger at the surface compared to the base of the feature, resulting in preferential fiber deposition on the mold surface relative to within the microneedle cavities.

It was possible to exert spatial control of electrospun fiber deposition in order to integrate electrospun fibers with dissolving microneedles. The effect of various design parameters on electrospun fiber deposition onto microneedle molds is also described. The strategy for spatial control of electrospun fiber disposition is compatible with different fiber materials, which enables control over release properties in microneedle applications. The integrated fiber microneedles possess sufficient mechanical strength to puncture tissue, and the integrated fibers retain their ability to incorporate and release diverse biologics.

In several embodiments, an in situ integration approach was used to create a dissolving microneedle system that could deliver microneedles containing biodegradable electrospun fiber scaffolds into the skin. A custom-designed composite microneedle mold was fabricated and comprised of conductive polydimethylsiloxane (C-PDMS) cavities combined with a thin insulative PDMS surface layer to control the spatial deposition of electrospun fibers. This is illustrated in frames 'a' and 'b' of FIG. 7. PDMS was used as the bulk mold material because of its elasticity and capability for gas exchange, and because of its proven performance in microneedle fabrication designs. PDMS was made sufficiently conductive by incorporating carbon black nanoparticles. The addition of a thin insulating material on top of a conducting material was observed to sufficiently alter the potential of a substrate to control electrospun fiber deposition. A non-conductive and non-polar PDMS surface layer was used to increase the electric potential at the substrate surface enough to achieve selective deposition of electrospun fibers into the grounded microneedle cavities.

In some embodiments, the microneedle mold material is created in two steps. First, C-PDMS was formulated by mixing 7.5 wt % carbon black with PDMS. Before curing, it was placed in molds on a plate shaker for about 15 hours to allow the carbon black particles to settle towards the bottom of the mixture, establishing a local increase in carbon black concentration on one side of the C-PDMS. Settling of the carbon black induced by the shaking process made the material sufficiently conductive for electrospinning without the need for higher carbon black concentrations, e.g., greater than 30 wt %. Because high carbon black concentrations change the rheological properties of the PDMS, even distribution of carbon black in these mixtures required special mixing processes. PVA fibers were electrospun onto either the top or bottom side of the cured C-PDMS to observe the effect of the carbon black settling. The 7.5 wt % carbon black concentration was selected based on the approximately 1.6-fold increase in the number of microneedle cavities containing fibers compared to lower carbon black concentrations. Based on visual image inspection, the 7.5 wt % carbon black concentration also increased the amount of fibers in the microneedle cavities compared to lower concentrations and reduced surface fiber deposition compared to higher carbon black concentrations. In the second step of the mold material fabrication process, the cured C-PDMS is inverted and a thin layer of PDMS is added to the surface and cured to create a two-layer composite. This is illustrated by frame 'a' of FIG. 7.

Figure 7:
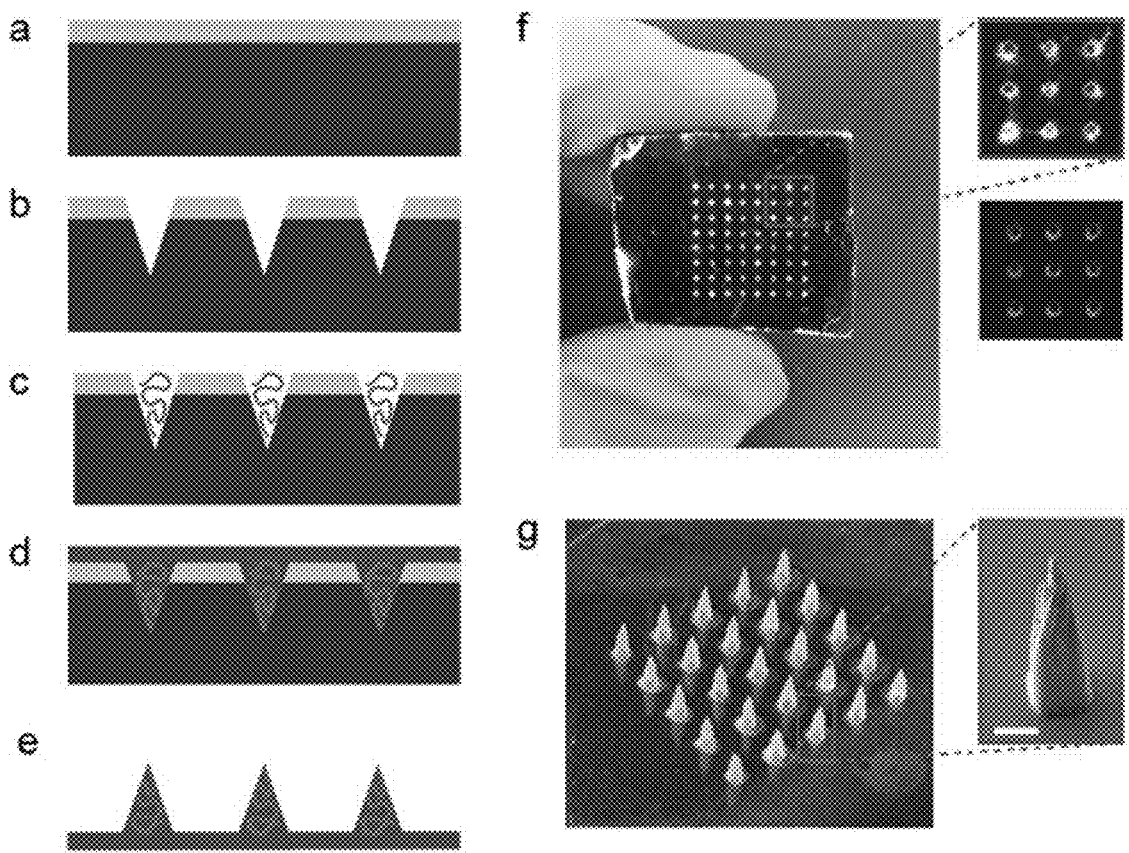
FIG. 7 is a schematic of an example process to integrate electrospun fibers into microneedles.

In this example embodiment, a laser cutter was used to create conical microneedle cavities in this two-layer composite material, as shown in frame 'b' of FIG. 7. The starting point for the laser cutter settings and designs were tailored for a specific laser cutter and materials to create microneedles with diameters ranging from 98 to 378 μm and heights ranging from 159 to 895 μm. The two-layer composite microneedle mold may then be used as a substrate for electrospinning, as shown in frame 'c' of FIG. 7. The mold was grounded and held in place using a custom holder that attached four copper wires into the back of the mold. The system is compatible with aqueous solutions of polyvinyl alcohol (PVA) and organic solutions of polycaprolactone (PCL) and poly(lactic-co-glycolic acid) (PLGA). Organic solution of PCL and PLGA were emphasized to ultimately harness their sustained release properties. Selective fiber deposition was observed within the microneedle cavities and not on the surface of the substrate, as shown in frame T of FIG. 7. This was due to an increased electric potential at the substrate surface caused by the insulative PDMS layer.

In some embodiments, a polymer backfill may then be applied to give the integrated fiber microneedles mechanical strength and to create a dissolvable backing layer, as shown in frame 'd' of FIG. 7. In this example embodiment, the microneedle cavities were filled with an aqueous poly (acrylic acid) (PAA) solution (8.75 wt %) by centrifugation at 1000×g for 1 hour, and then excess PAA was removed from the mold surface and a higher concentration PAA solution (35 wt %) was added to the mold to create a strong backing layer. Microneedles were dried at room temperature for 2 days, and then the complete integrated fiber microneedle device was gently removed from the PDMS mold, as shown in frames 'e' and 'g' of FIG. 7. Once the mold was fabricated, the integrated fiber microneedles were able to be fabricated with an active time of approximately 1 hour. The resulting arrays are flexible and delaminated easily from the mold.

Frame 'a' of FIG. 7 shows cured composite material containing a PDMS surface layer on top of C-PDMS. Frame 'b' shows conical cavities that were micromachined into the two-layer composite using a $CO_2$ laser. Frame 'c' shows polymer fibers that were electrospun directly into the microneedle cavities. Frame 'd' shows a hydrophilic polymer backfill added to the mold under vacuum to add mechanical strength and create a backing layer. Frame 'e' shows integrated fiber microneedles after being removed from the mold. Frame 'f' is a representative image of PVA fibers electrospun directly onto the two-layer composite microneedle mold showing preferential accumulation of the white fibers into the black cavities of the mold (inset: microneedle mold with and without fibers). Frame 'g' is a representative SEM image of a single integrated fiber microneedle after removal from the PDMS mold. Scale bar: 200 μm.

The ability to integrate fibers into a range of microneedle dimensions demonstrated the broad applicability of this new delivery platform. Different needle dimensions may be used to access different tissue depths or to puncture tissues with different mechanical properties. A PDMS surface shielding strategy was selected, enabling selective fiber deposition into a range of microneedle cavity geometries. This selection and its enabling effect was evaluated using a two-dimensional COMSOL electrostatic model and then verified experimentally.

Electrospun fibers are extremely sensitive to minor changes in electric field and collector dielectric properties. Fiber deposition can be focused into centimeter scale spot sizes through manipulation of the electric field, and fiber collection density can be modified on the micrometer scale by micropatterned collectors.

Figure 8:
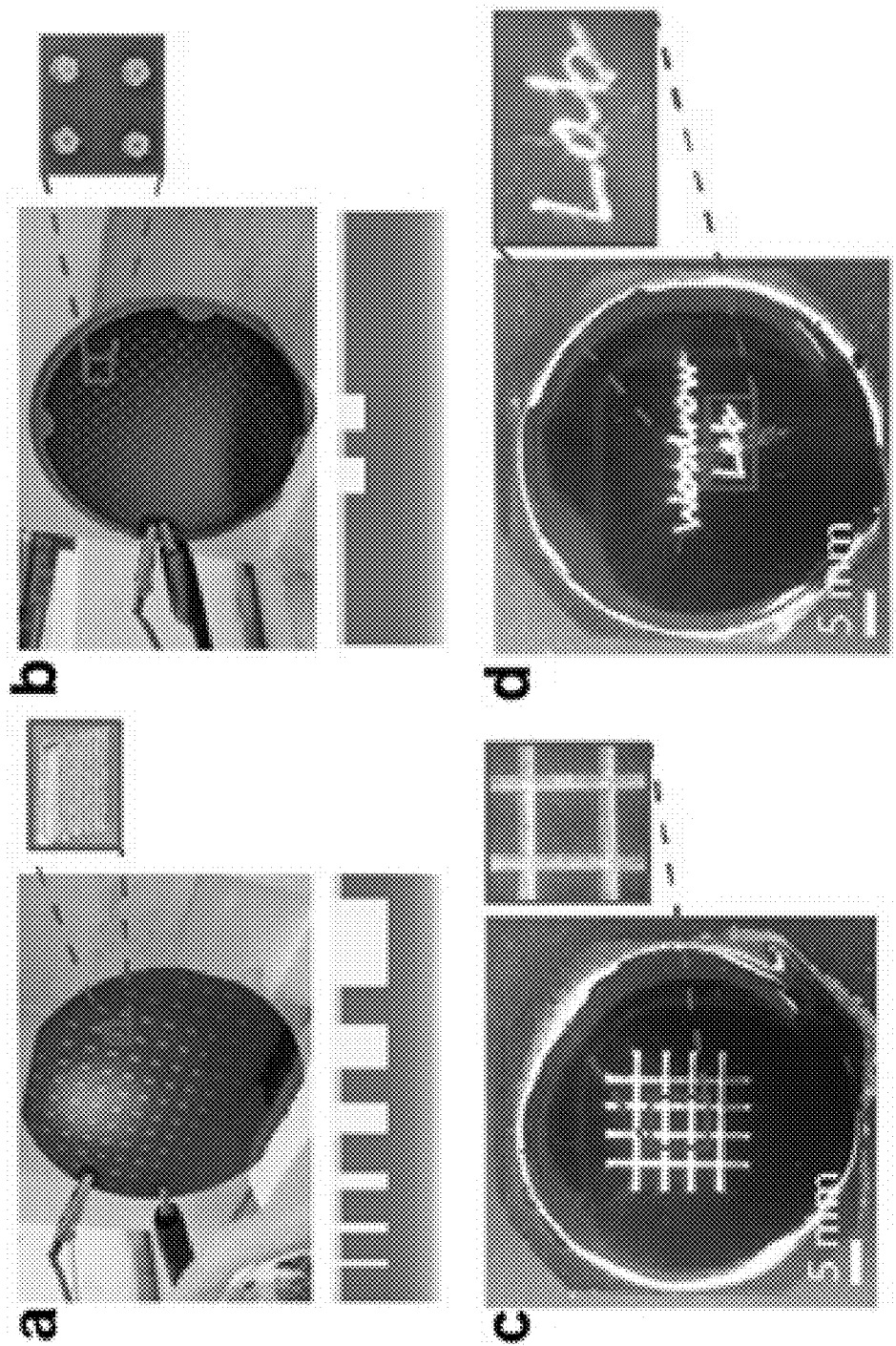
FIG. 8 illustrates deposition of fibers on example substrates.

The ability of collectors with an insulative surface layer and conductive recessed patterns to generate three-dimensional patterned fibers on a range of length scales was investigated. To evaluate this concept, micropatterned collectors in silicon were created. Trench patterns with 150-μm depth and doughnut patterns with 50-μm depth were created in silicon wafers using standard photolithographic patterning and deep reactive ion etching. The approximately 2-μm thick polymeric photoresist was left on the wafer after etching, creating a two-layer patterned collector with an insulative surface layer. This is shown in frames 'a' and 'b' of FIG. 8. Poly(vinyl alcohol) (PVA) fibers were readily deposited over the majority of the collector, and fibers deposited more densely in the silicon patterns than on the photoresist-coated collector surface. This effect may be related to an increase in electric potential at the collector surface, leading to fiber repulsion from the surface and deposition in the conductive recessed patterns.

Poly(dimethyl siloxane) (PDMS)-based collectors were also created. PDMS is easy to manipulate on a range of length scales using either additive or subtractive methods. Additionally, PDMS can be made conductive by incorporating high concentrations of conductive particulates such as carbon black. A conductive mixture of carbon black and PDMS (C-PDMS) was created, then an approximately 600-µm thick layer of insulative PDMS was added on the surface of the conductive layer. Use of this material enabled rapid fabrication of complex patterns on the scale of hundreds of micrometers using a $CO_2$ laser. Similar to the silicon collectors, PVA fibers deposited more densely within the patterns compared to the collector surface. This is shown in frames 'c' and 'd' of FIG. 8. Together, these preliminary experiments demonstrate that patterned conductive collectors with an insulative surface layer can be used to generate patterned electrospun fibers on a range of length scales.

The design space of this fiber patterning strategy was evaluated using a series of two-dimensional finite element method simulations. The first set of simulations followed a two-level, five factor, full factorial design to determine collector design factors that would have the most significant effect on electrospun fiber patterning. Factors of interest included insulative layer thickness and feature spacing, width, height and geometry (see frame 'a' of FIG. 9). The primary response output was the difference between the electric field at the bottom of the pattern and the electric field at the collector surface ($\Delta E$). Assuming the deposition of the electrospun fibers is primarily driven by the force of the electric field, a $\Delta E$ greater than 0 would predict more fiber deposition in the patterns compared to the collector surface.

Each simulation calculated the potential and electric field for geometries, materials, and electrostatic conditions matching actual experimental setups to be used in later studies. These setups are illustrated in frames 'b' and 'c' of FIG. 9. Two sample simulations for small scale (2.5 mm width, height, spacing, and thickness) and large scale (7.5 mm width, height, spacing, and thickness) square patterns computed a $\Delta E$ of −143 V/m for the small scale pattern and a higher $\Delta E$ of 105 V/m for the large scale pattern, as shown in frames 'b' and 'c' of FIG. 9. To determine the factor or factors that were driving this result, the main effect size for each factor was calculated. The main effect for each factor is defined as the difference between the average $\Delta E$ at its high and low levels holding all other factors constant. For this set of experiments, the insulative layer thickness and feature height had the largest effect on $\Delta E$ (effect size=1,615 and −1,632 V/m, respectively); this is shown in frame 'd' of FIG. 9. These results indicate that an increase in insulative layer thickness or a decrease in feature height would result in an increased $\Delta E$, which predicts increased fiber deposition in the pattern. Calculation of two- and three-factor interactions showed that only the interaction of insulative layer thickness and feature height had an appreciable effect on $\Delta E$ (effect size=−1,424 V/m). Because these two factors interact, their effect should be considered by the interaction term rather than the individual main effects. Statistical analysis showed that all of the evaluated factors and the thickness-height interaction factor had a significant effect on $\Delta E$. However, it was also clear from this analysis that $\Delta E$ is primarily determined by the thickness-height interaction. These results suggest that appropriate selection of just feature height and insulative layer thickness can yield electrospun fiber patterns of a variety of widths, spacing, and shape with high selectivity.

Frame 'a' of FIG. 9 shows a P-diagram of the design of experiments, including the five different control factor inputs and the primary response output. Factors were varied from 2.51 mm to 7.51 mm in the initial full factorial design, then were varied from 0.01 mm to 10.01 mm for the central composite design. Representative images from two distinct simulations for square feature geometry with 2.51 mm width, height, spacing, and thickness (shown in frame b'), and 7.51 mm width, height, spacing, and thickness (shown in frame 'c'). These images show the starting geometry, the calculated electric potential (color gradient, scale in kV), and electric field (arrow vectors). Annotations indicate the location of the collector surface (*) and bottom of the pattern (^) used to calculate the $\Delta E$ response output. Frame 'd' is a means plot showing the relative effect of each factor at each level. The largest effect was observed for the insulative layer thickness, feature height, and the interaction of these two factors. Frame e' shows a heat map of $\Delta E$ from the quadratic model that indicates that $\Delta E$ is maximized by limiting feature height to 5 mm and increasing the insulative layer thickness proportionally with increasing feature height.

To further explore factor interactions and to evaluate a larger range of pattern dimensions, another set of simulations was conducted following a central composite experimental design. Shape was omitted as a factor to simplify the design and because the full factorial design indicated that it was not one of the main factors affecting $\Delta E$. The results were similar to the results from the full-factorial design, with the largest and most significant effects observed for insulative layer thickness, feature height, and the interaction of these two factors. A quadratic model based on the results was then used to construct a heat map of the interaction between insulative layer thickness and feature height for intermediate values of spacing (5 mm) and width (5 mm). This heat map indicated that to maximize $\Delta E$ for the dimensions evaluated here, feature height should be limited to 5 mm and insulative layer thickness should be increased proportionally as feature height increases (see frame 'e' of FIG. 9). Importantly, $\Delta E$ can be increased for feature heights greater than 5 mm by further increasing the insulative layer thickness beyond the range of these simulations. For example, $\Delta E$ of 2,581 V/m was calculated for a triangular feature with 5.01 mm width, 15 mm height, 5.01 mm spacing, and 20 mm insulative layer thickness. Together these simulations show that this fiber patterning strategy can be used over a wide range of length scales.

These simulation results were validated experimentally. The first goal of the experimental evaluation was to assess the effect of the insulative surface layer compared to a fully conductive patterned collector. An additive strategy was used to generate millimeter-scale patterns (3 mm diameter, 3.25 mm height, and 5.5 mm spacing) in a collector with and without a 600-µm thick insulative PDMS layer. This is shown in frames 'a' and 'b' of FIG. 10. PVA fibers deposited only on the surface of the fully conductive collector without the insulative layer, but fibers deposited densely in the patterns on the insulated two-layer collector. These results are in agreement with the simulations, which calculated a 365 V/m higher $\Delta E$ for the collector with the insulative PDMS layer. These studies experimentally demonstrate the function of an insulative surface layer to achieve fiber deposition within recessed patterns.

The PDMS-based collectors were then scaled down by approximately 10-fold to verify that the patterning effect was valid at smaller length scales (conical pattern: 269±5 µm diameter, 522±6 µm height, 1400 µm spacing, 400 µm insulative PDMS layer thickness). Based on the simulations (ΔE=882 V/m), fiber deposition was anticipated in the patterns for this collector. A similar patterning effect was observed for this microscale collector, with fibers deposited densely within the patterns in 1-2 minutes and little to no deposition on the collector surface, as shown in frame 'c' of FIG. 10. To verify that this was not simply fibers bridging over the patterns, the electrospinning time was increased to create a fiber mat strong enough to be removed from the collector. The fibers were then imaged with scanning electron microscopy; it was observed that the fibers conformed to the patterned collector in three dimensions (as seen in frame 'd' of FIG. 10). Coupled with the results for the millimeter-scale collector, these results confirm that with appropriate selection of feature height and insulative layer thickness, the fiber patterning strategy is feasible on a range of length scales.

To better understand the effect of insulative layer thickness on fiber deposition, a microscale collector was fabricated with a gradient insulative PDMS layer thickness and constant feature geometry, dimensions, and spacing. This collector contained conical patterns (364±16 µm diameter, 777±20 µm height, 1600 µm spacing), and an insulative PDMS layer that ranged from 400 to 580 µm. Simulations calculated that the ΔE ranged from 647 V/m for the 400 µm PDMS thickness to 705 V/m for the 580 µm PDMS thickness. PVA fibers were deposited densely in the patterns over a majority of the collector in 1-2 minutes, with more visible fibers in the patterns with a thinner insulative PDMS layer and fewer visible fibers visible in patterns with a thicker insulative PDMS layer (see frame 'e' of FIG. 10). When cross-sections of this fiber-containing collector were inspected by SEM, it was observed that the fiber deposition depth was modulated by the insulative PDMS thickness. Fibers deposited near the openings of the patterns with a 400 µm thick PDMS layer (as shown in frame 'f' of FIG. 10), while fibers appeared to be deposited toward the bottom of the pattern for a 500 µm-thick PDMS layer (as shown in framge 'g' of FIG. 10). The deeper fiber deposition in patterns with a thicker insulative PDMS layer is possibly related to the increased ΔE compared to patterns with a thinner insulative PDMS layer.

Overall, the experimental evaluation of these two-layer collectors for in situ fiber patterning agreed with the predictions of the finite element method simulations. Electrospun fibers deposited into patterns with a range of feature heights from 3.25 mm to 522 µm through appropriate selection of insulative layer thickness, corroborating a key finding from the simulations. Because the simulations do not capture some key factors related to fiber material and electrospinning dynamics, they cannot be used alone to precisely determine fiber deposition patterns. However, agreement in trends between the experiments and the simulations suggests that the simulation results can be used as a guide to direct the design of two-layer collectors for three-dimensional patterning of electrospun fibers.

Figure 10:
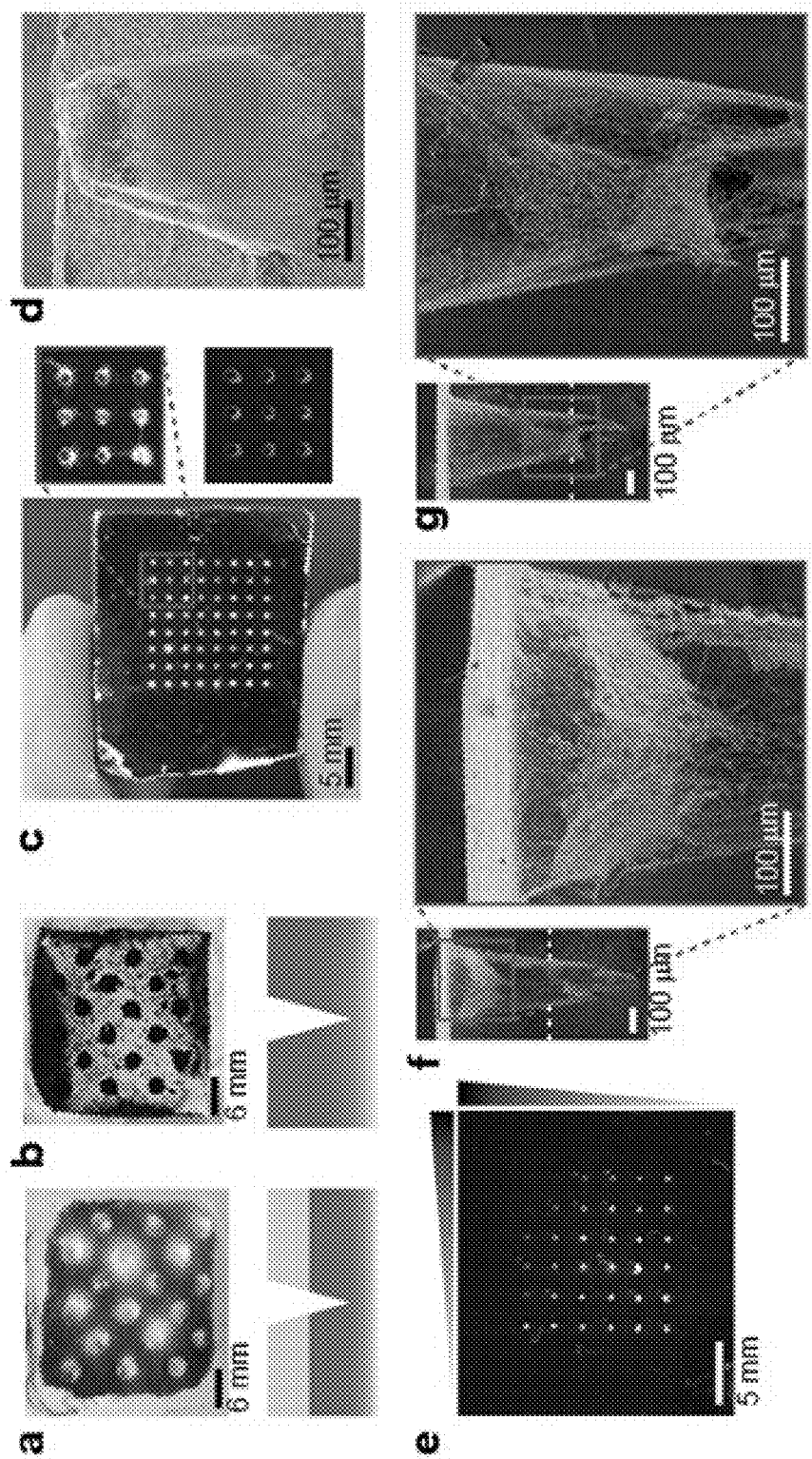
FIG. 10 illustrates fiber deposition results from a range of deposition parameters.

PVA fiber collection on millimeter-scale PDMS-based patterned collectors is shown in frame 'a' with and in frame 'b' without a 600 µm thick PDMS surface layer demonstrates the need for the insulative layer to achieve fiber deposition in the micropatterns. Conical patterns had diameter 3 mm, 3.25 mm height, and 5.5 mm spacing. Frame 'c' of FIG. 10 shows a micro-scale PDMS-based collector with (top inset) and without (bottom inset) PVA fiber deposition. Collector had 400 µm PDMS thickness and conical patterns with 269±5 µm diameter, 522±6 height, 1400 µm spacing. Frame 'd of FIG. 10 shows an SEM image of fibers carefully removed from micro-scale collector demonstrates fiber patterning in three dimensions. Frame 'e' of FIG. 10 shows a top-down view of micropatterned collector with gradient PDMS layer thickness containing PVA electrospun fibers. This collector contained conical patterns with 364±16 µm diameter, 777±20 µm height, 1600 µm spacing, and a PDMS layer that ranged from 400 to 580 µm. Fiber deposition is less visible in areas of the collector with thicker PDMS layer. Frame 'f' of FIG. 10 shows a cross-sectional SEM image of the gradient PDMS thickness micropatterned collector at a region with 400 µm PDMS thickness and frame 'g' shows a region with 500 µm PDMS thickness containing PVA electrospun fibers. The approximate location of the insulative layer is denoted by the white dashed line. These SEM images were processed in Adobe Photoshop to improve visibility of fibers. Contrast was set to 100 and exposure offset was set to −0.1. For all electrospinning experiments, the needle-collector separation distance was 10 cm. The solution flow rate varied between 1.5-5 µL/min and the applied voltage varied between 7.5-8.5 kV because of the differences in solution properties. For millimeter scale collectors, fibers were electrospun for approximately 5 minutes, and for microscale collectors, fibers were electrospun for 1-2 minutes.

Another desirable feature of this patterning strategy is its ability to accommodate in situ electrospinning of a variety of fiber materials with different physicochemical properties. This was evaluated experimentally since the properties of the fibers and their behavior in the electric field are complex and difficult to simulate accurately. Patterning of polycaprolactone (PCL) and poly(lactic-co-glycolic acid) (PLGA) were demonstrated because they are widely used in drug delivery and tissue engineering, and organic solutions of these polymers have very different properties than the aqueous PVA solution used in earlier experimental validation studies of these methods. Because the PDMS-based collectors are much less conductive than standard metal collectors used for electrospinning, the low polarity polyester solutions required optimization to identify formulations with reproducible results, high yield, and selectivity for the pattern. For each polyester, solution properties and fiber output were measured from electrospinning (2 minutes) onto a collector containing five 2×6 arrays of conical patterns (364±16 µm diameter, 777±20 height, 500-4000 µm spacing, 500 µm insulative layer thickness). The yield and the experimental fiber selectivity ($S_E$) were also measured, defined here as the ratio of fiber mass deposited in the patterns to fiber mass deposited on the collector surface (as shown in Table 1 and frame 'a' of FIG. 11).

To improve the in situ patterning of PCL fibers, PCL solutions at 12 wt % in various solvents and solvent mixtures were prepared with different conductivity and viscosity, factors that can affect fiber morphology and deposition patterns. In general, higher fiber yield was observed for PCL solutions with higher viscosity and lower conductivity (chloroform (CHL), 3:1 chloroform:dimethylformamide (CHL:DMF)) (Table 1). The CHL:DMF mixture was prioritized for further studies because of its high $S_E$ combined with its high yield and uniform deposition across the collector (shown in frame 'a' of FIG. 11). In the next iteration of PCL solution development, the solution conductivity was tuned by changing the ratio of CHL:DMF rather than through addition of salts because of the poor yield and $S_E$ of the highest conductivity solutions in the initial solvent evaluation (Table 1). The best yield (100.8%) and $S_E$ (4.9) were observed for the PCL solution in 5:1 CHL:DMF, which had approximately 30% lower conductivity and approximately 20% higher viscosity than the starting 3:1 CHL:DMF solution (as shown in frame 'b' of FIG. 11). While the yield of this solution still varied between replicates, $S_E$ was reproducible. Ultimately, a 12 wt % solution of PCL in 5:1 CHL:DMF was identified to be best suited for in situ patterning, producing a nearly 20-fold increase in fiber yield and nearly 50-fold increase in $S_E$ compared to the worst performing solution. A similar approach was used to identify a formulation with high yield and $S_E$ for PLGA fibers. Here, it was found that a 10% PLGA solution in CHL provided the best yield (111%) and $S_E$ (6.71) (shown in frame 'c' of FIG. 11). Performance of PLGA solutions followed similar trends to the PCL solutions, with higher viscosity and lower conductivity solutions producing the highest $S_E$ and yield (Table 1). The polymer solution development performed here provides a framework for adapting any fiber formulations containing active agents, other additives, or different fiber materials for use with the patterning strategy disclosed herein.

Figure 11:
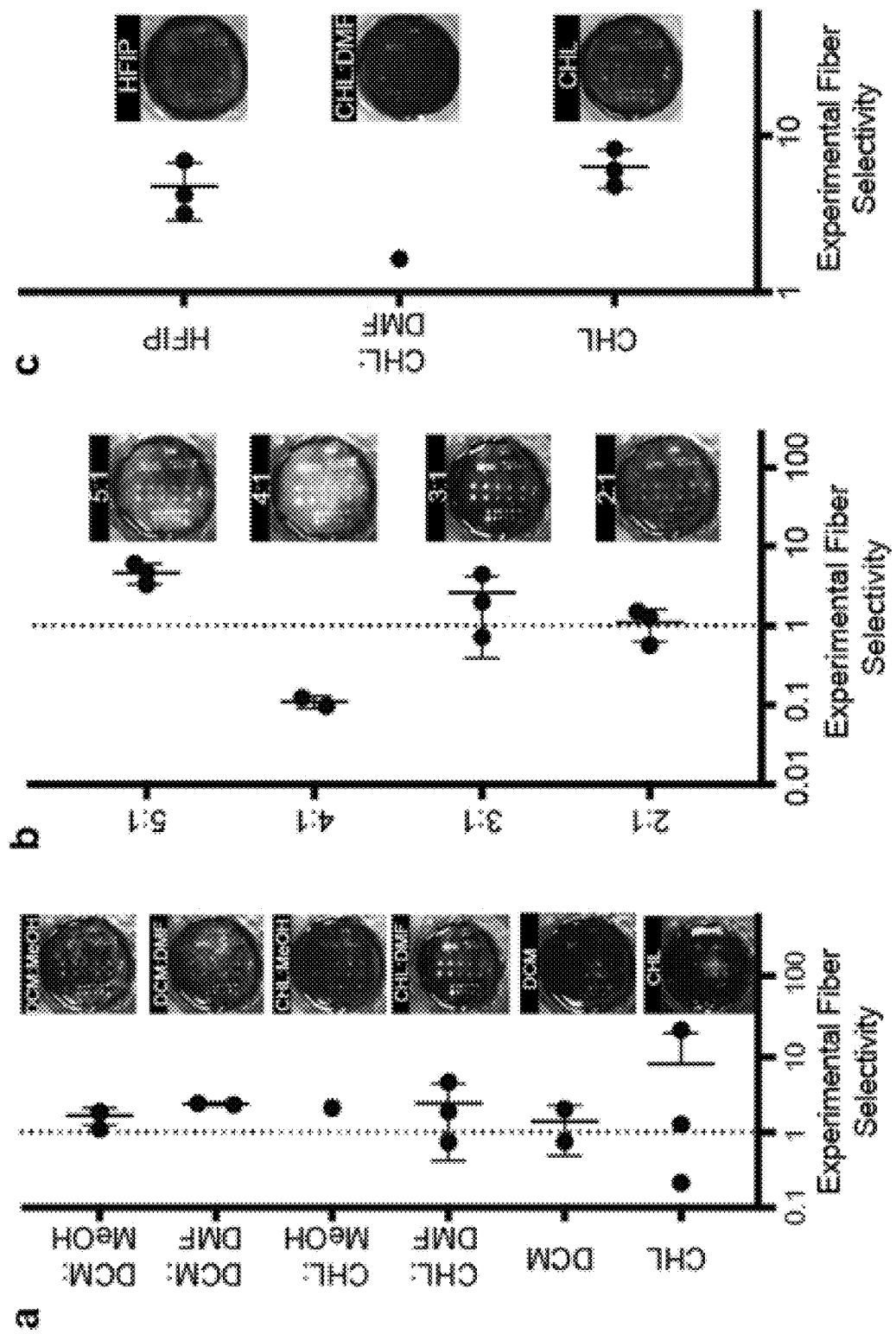
FIG. 11 illustrates fiber deposition results from a range of fiber solution compositions.
Figure 12:
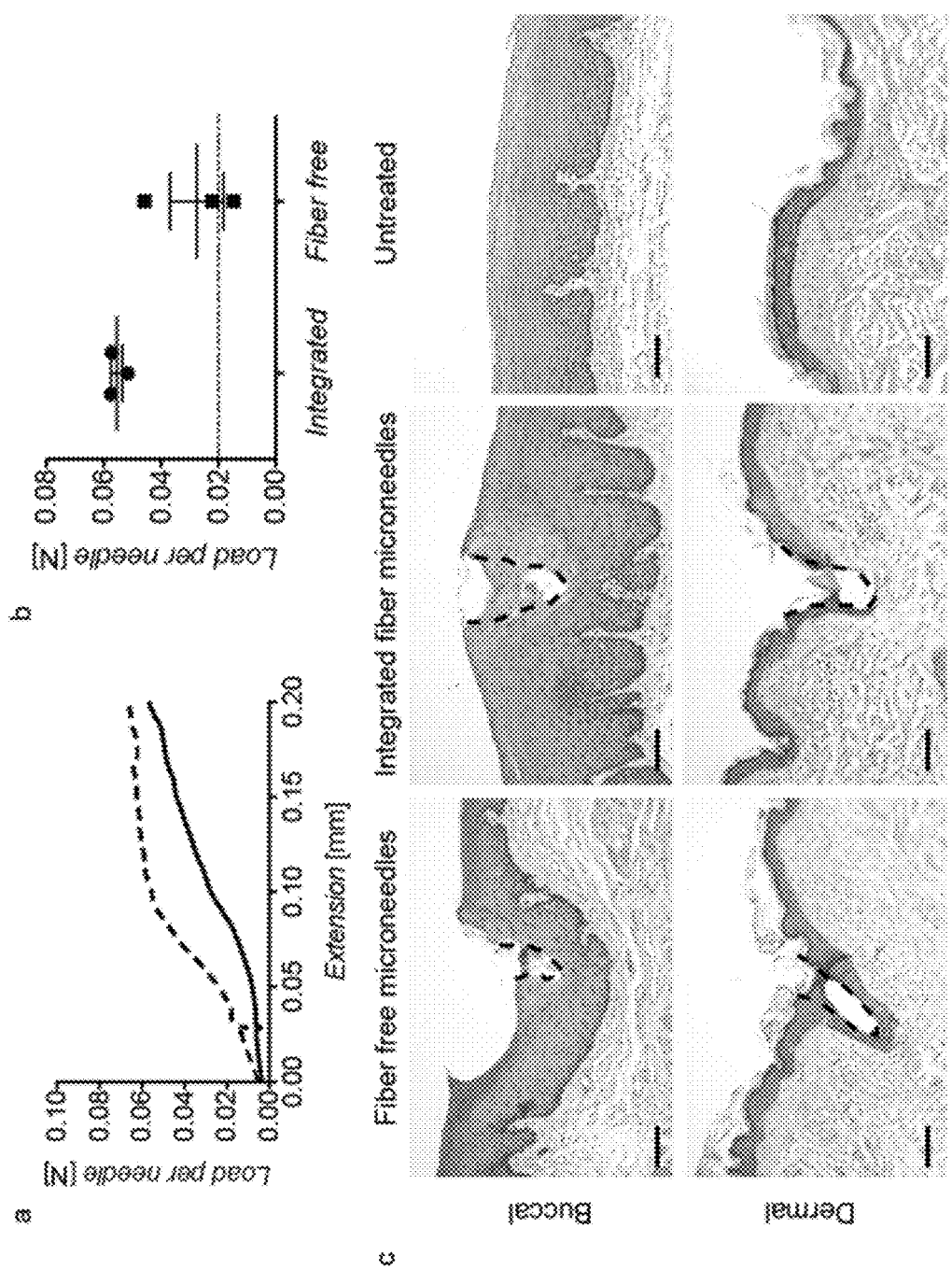
FIG. 12 illustrates needle penetration results.

FIG. 11 shows the relationship between the ratio of fiber mass in the micropatterns to fiber mass on the collector surface and representative top-down images of fibers on micropatterned collectors for PCL fibers electrospun from different solvents (frame 'a'), PCL fibers electrospun from different CHL:DMF ratios (frame 'b'), PLGA fibers electrospun from different solvents (frame 'c'). (n=3, error bars represent standard deviations). The same collector with conical micropatterns of base diameter 364+16 μm, height 777+20 μm, spacing ranging from 0.5 mm to 4 mm, and insulative layer thickness 0.4 mm was used for all electrospinning experiments. PCL fibers were electrospun at a voltage of 17 kV, while PLGA fibers were electrospun at a voltage of 18 kV. All fiber samples were electrospun at a 5 μL/min flow rate and 25 cm tip to collector distance for 2 minutes.

the graph of extension as a function of load, as shown in frame 'a' of FIG. 12. Measured integrated fiber microneedle failure forces exceeded previously established targets for tissue puncture, with an average failure force per needle of 0.055 N, as shown in frame 'b' of FIG. 12. This failure force was very reproducible from batch to batch, suggesting a consistent process. Since the predicted force per needle for tissue insertion is approximately 0.02 N, these needles have a factor of safety of nearly 3, meaning reliable and complete tissue puncture is expected. Interestingly, when solid polymer microneedles were prepared without fibers using the same procedure used for the integrated needle backfill, these needles were observed to have failed at a lower force of 0.027 N/needle. This suggests that the fibers may act as reinforcement to prevent needle failure.

To validate that the integrated fiber microneedle device could effectively puncture tissue, puncture in non-human primate dermal and buccal tissue was demonstrated. These tissues are of interest for drug and vaccine delivery, and possess different mechanical properties. Integrated fiber microneedles were hypothesized to be sufficiently sharp and strong to effectively penetrate both tissues. The results indicate that integrated fiber microneedles were sufficiently strong to breach the stratum corneum and the viable epidermis of dermal tissue, as shown in frame 'c' of FIG. 12. This result accords with the compression data for the fiber free microneedles, which indicated a 3-fold lower failure force for fiber free microneedles compared to integrated fiber microneedles. In buccal tissue, the integrated fiber microneedles penetrated to a depth of 242 μm, 30% of the needle height. Meanwhile, fiber free microneedles penetrated only 130 μm in the buccal tissue, potentially because they are mechanically weaker than the integrated fiber microneedles.

Frame 'a' of FIG. 12 is graph of load and extension per needle for microneedle compression on an Instron load frame. Curve represents the mean of three integrated fiber microneedles (dashed line) and fiber free microneedles (solid line) from separate substrates. Error bars omitted for graph clarity. Frame 'b' shows compiled failure forces per needle for integrated fiber microneedles compared to fiber free microneedles. For all samples measured with this method, the failure force was taken as the load at 0.1 mm

TABLE 1

Polymer solution properties for patterned electrospun fibers

| | Solvent | Conductivity (μS/cm) | Viscosity (Pa*s) | Output (mg)[a, b] | Yield (%)[a] | $S_E$ |
|---|---|---|---|---|---|---|
| PLC Solvent Selection[c] | CHL | 0.00 | 6.66 | 0.55 ± 0.32 | 45.8 ± 26.6 | 8.09 |
| | DCM | 0.00 | 3.45 | 0.1 ± 0.01 | 8.3 ± 0.8 | 1.39 |
| | DCM:DMF | 0.59 | 5.54 | 0.35 ± 0.25 | 29.1 ± 20.8 | 2.38 |
| | DCM:MeOH | 0.81 | 2.64 | 0.14 ± 0.07 | 11.6 ± 5.8 | 1.67 |
| | CHL:MeOH | 0.56 | 2.58 | 0.07 ± 0.04 | 5.8 ± 3.3 | 2.11 |
| | CHL:DMF | 0.24 | 4.56 | 0.83 ± 0.39 | 69.1 ± 32.5 | 2.43 |
| PLC Conductivity Evaluation[c] | 2:1 CHL:DMF | 0.22 | 3.91 | 0.57 ± 0.32 | 47.5 ± 26.6 | 1.09 |
| | 4:1 CHL:DMF | 0.20 | 5.33 | 0.76 ± 0.26 | 63.3 ± 21.6 | 0.10 |
| | 5:1 CHL:DMF | 0.17 | 5.36 | 1.21 ± 0.49 | 100.8 ± 40.8 | 4.90 |
| PLGA Solvent Selection[d] | CHL | 0.00 | 2.03 | 1.11 ± 0.16 | 111 ± 16 | 6.71 |
| | CHL:DMF | 0.36 | 3.72 | 0.17 ± 0.08 | 17 ± 8 | 2.06 |
| | HFIP | 0.09 | 10.84 | 1.04 ± 0.40 | 104 ± 40 | 5.21 |

[a]Mean ± standard deviation of n = 3 electrospinning replicates,
[b]Output is reported as total fiber mass on the collector after 2 minutes of electrospinning,
[c]All PCL solutions were prepared at 12 wt %,
[d]All PLGA solutions were prepared at 10 wt %

How fiber integration affected the mechanical properties of the microneedles was studied. Compressive testing suggested that integrated fiber microneedles were stiffer than fiber free microneedles, measured by the higher slope from extension. Frame 'c' shows optical microscopy of dermal and buccal tissue treated with fiber free microneedles or integrated fiber microneedles demonstrating integrated fiber microneedle disruption of the dermal stratum corneum and viable epidermis and fiber free microneedle and integrated fiber microneedle access to the epithelium of buccal tissue. Untreated dermal and buccal tissue controls are provided to demonstrate the native structure of both tissues. Scale bar: 100 µm.

A small molecule drug, a model protein, and plasmid DNA were loaded into individual devices and the release kinetics of each were measured. These agents were loaded into an array of 420 needles, with a total device size of 4.2 cm$^2$. In this experiment, the needles were 350 µm in diameter and 800 µm tall. The microneedles had a center-to-center spacing of 1 mm and the PDMS surface layer was 500 µm. Each agent was successfully loaded into the fiber-microneedle system using a loading of 100 µg for the small molecule, 52 µs for the protein, and 1.1 µg for the DNA. The release of the small molecule tenofovir (TFV), bovine serum albumin (BSA), and plasmid DNA showed a sharp initial burst release followed by a plateau, as shown in frames 'a,' 'b,' and 'c' of FIG. 13. This plateau occurred at different percent release for the different agents. The small molecule plateaued at 70% release, the protein plateaued at 35% release, and the plasmid DNA plateaued around 80% release. The differences in release kinetics for the small molecule compared to the protein are likely due to molecule size, where the TFV can easily diffuse out of the fibers and into the release media, while the larger protein is more entrapped in the fiber. The DNA likely reached a more complete release during this initial time period because of the excipients that were incorporated in the fibers to protect the DNA during the electrospinning process. These excipients could have increased the porosity of the fibers, therefore increasing the amount of DNA release.

The loading achieved here is modest, but could be increased through optimization of the fiber formulations. The observation that the release kinetics were generally similar to what has previously been observed for the PCL fiber system suggests that when other fiber systems are incorporated into the integrated fiber microneedles, the device will demonstrate similar control over release profiles as fibers alone.

Figure 13:
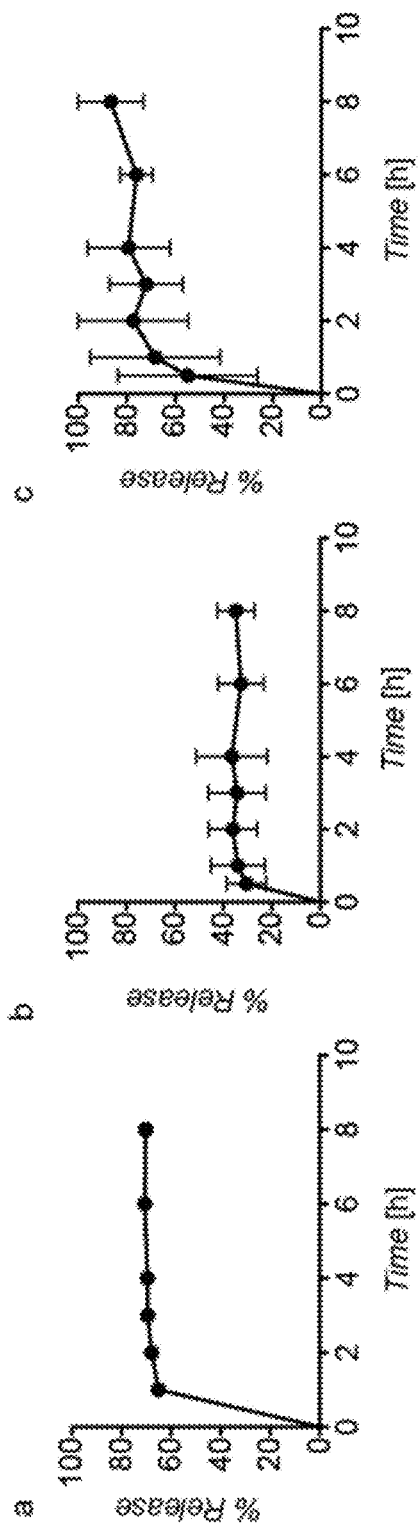
FIG. 13 illustrates controlled release of substances from microneedles.

Frame 'a' of FIG. 13 shows release of a small molecule antiretroviral drug, tenofovir (TFV), measured by HPLC. Data represent release from a single array of integrated fiber microneedles. Complete (100%) release was determined by TFV detected in release media after 84 days. Frame 'b' shows release of a model protein, bovine serum albumin (BSA), measured by BCA assay. Data represent two replicates from separately fabricated arrays of integrated fiber microneedles. Complete (100%) release was determined by the theoretical encapsulation of BSA in the iFMD. Frame 'c' shows release of plasmid DNA, measured by spectrophotometry. Data represent two replicates from separately fabricated arrays of integrated fiber microneedles. 100% release was determined by DNA detected in release media after 25 days.

Design and preparation of two-layer composite microneedle molds: the effect of various two-layer composite microneedle mold designs on the electric field near the mold was evaluated using finite element method simulations (COMSOL Multiphysics version 5.1). The 2D schematic of the mold and the electrospinning setup for each simulation was prepared in AutoCAD (Autodesk AutoCAD 2015). For every simulation, the tip to substrate distance was set to 10 cm and the applied voltage was 7.5 kV. To prepare the two-layer composite microneedle molds, C-PDMS was prepared by first incorporating 7.5 wt % carbon black (Vulcan XC 72R) into the PDMS pre-polymer (Sylgard 184, Dow Corning) using an overhead stirrer (IKA Eurostar) with a propeller attachment at 250 rpm. When all the carbon black was incorporated, the PDMS curing agent (1:10 ratio to the pre-polymer) was added and mixed for 5 minutes at 250 rpm. C-PDMS was added to plastic weigh boats and placed on a rotating platform shaker at the highest setting for at least 15 hours. C-PDMS was then cured in an oven at 37° C. for 24 hours. Finally, the C-PDMS materials were flipped over, and PDMS (0.4 mL) was added to the surface. All laser cutting was performed on a VLS 3.60 system (Universal Laser Systems) in vector mode with the enhance feature selected. To create the 350 µm diameter base and 800 µm height microneedles, a helix pattern with 10 turns and a diameter of 0.25 mm was plotted using the laser cutter. Laser power was set to 40% and speed was set to 90%.

Polymer solution preparation and electrospinning: solutions of polyester materials were prepared by combining PCL (Sigma Aldrich, average Mn 80,000) or PLGA (Lactel Absorbable Polymers, 50:50 L:G ester terminated, 0.55-0.75 dL/g inherent viscosity in HFIP) in appropriate solvents, followed by stirring overnight on a rotisserie style shaker at room temperature. Solutions of PVA (Spectrum Chemical, Mw-105 kDa, P1180) were prepared in water by stirring overnight with gentle heating. Polymer solution conductivity was determined using a conductivity meter (Thermo Scientific Orion Star A212) and viscosity was measured on a rheometer (TA Instruments AR-G2). For blank integrated fiber microneedles, polymer solutions were loaded in a glass syringe fitted with a 22G blunt tipped needle. TFV (40% w/w) was loaded into the fibers by direct mixing in the polymer solution. BSA (150 µg) or DNA (1 m) was incorporated through an emulsion strategy, where 0.2% (v/v) Tween 20 was mixed into the polymer solution followed by drop-wise addition of the BSA- or DNA-containing aqueous phase with constant stirring. The polymer solution was dispensed from the syringe using a syringe pump (New Era Pump Systems, Inc.) with a 3 µL/min flow rate. The two-layer composite microneedle mold of interest was fixed to a custom holder that attached copper wires to the back of the mold. The wires were pierced through a polyethylene foam block to hold the mold at the proper height and to prevent fiber deposition on objects other than the mold. The ground from the power source (Gamma High Voltage Research) was attached to these wires and the positive lead was attached to the base of the needle. The applied voltage varied between 7.5 and 10 kV depending on the polymer solution. When the electrospinning was complete, the microneedle cavities were filled with an aqueous PAA solution (8.75 wt %) by centrifugation at 1000×g for 1 hour. Excess PAA was removed from the mold surface and a higher concentration PAA solution (35 wt %) was added to the mold to create a strong backing layer. Microneedles were dried at room temperature for 2 days, and then the complete integrated fiber microneedle device was gently removed from the PDMS mold.

Microneedle characterization: SEM imaging of electrospun fibers on the two-layer composite microneedle molds and completed microneedles was performed on a JEOL JSM7400F cold field emission scanning electron microscope. All samples were coated with a 3 nm layer of gold-palladium prior to imaging to prevent charging. Compression testing of microneedle arrays was performed on an Instron Universal Testing System (Model 5943) at a rate of 0.01 mm/s. An array size of 3×3 was used for all groups and replicates. Rhesus macaque buccal and dermal tissue was obtained from the Washington National Primate Research Center tissue donor program. Freshly excised buccal tissue was briefly dried with a Kimwipe, then either fiber free microneedles or integrated fiber microneedles were applied to the tissue with appropriate force for 30 seconds, followed by incubation at 37° C. for 5 minutes to allow device dissolution. Dermal tissue was shaved before harvesting, and treated in the same way. Tissues were rinsed with PBS, then fixed in formalin overnight. Fixed tissues were embedded in paraffin and sectioned on a microtome followed by hematoxylin and eosin staining to visualize the tissue microarchitecture. Release studies were performed by placing integrated fiber microneedles containing known amounts of TFV, BSA, or plasmid DNA into individual scintillation vials with appropriate amounts of PBS (TFV: 5 mL, BSA: 3 mL, DNA: 1 mL). At predetermined time points (1 h, 2 h, 4 h, 8 h, 10 h, 1 d, 2 d, 4 d, 7 d), release media was sampled and replaced. For TFV and BSA release, 200 uL samples were taken, while for DNA release, 20 uL samples were taken. TFV samples were filtered using a 0.2 µm PVDF filter prior to analysis. TFV content was determined by HPLC (Shimadzu Prominence LC20AD UV-HPLC) with a Phenomenex Luna 153 C18 column and LCSolutions software. The isocratic mobile phase contained 72% water with 0.045% trifluoroacetic acid (TFA) and 28% acetonitrile with 0.036% TFA. Each sample (20 µL) was injected into the system with a flow rate of 1 mL/min for 10 minutes total. The column was heated to 30° C., and TFV was detected at 259 nm. BSA content was analyzed by the Pierce MicroBCA Assay. The standard curve for the assay was prepared in PBS with 1 mg/mL PAA to control for background signal from the polymer. DNA content was determined by a Nanodrop 3300 Spectrophotometer. DNA was stained with Hoechst 33258 following the protocol for Hoechst Dye 33258 Assay for dsDNA from Thermo Scientific. DNA concentration was determined using a standard curve, and PAA-containing DNA controls were used to account for any change in fluorescence due to interference of these materials or pH changes

VI. Conclusion

The above detailed description describes various features and functions of the disclosed systems, devices, and methods with reference to the accompanying figures. In the figures, similar symbols typically identify similar components, unless context indicates otherwise. The illustrative embodiments described in the detailed description, figures, and claims are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the message flow diagrams, scenarios, and flowcharts in the figures and as discussed herein, each step, block and/or communication may represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages may be executed out of order from that shown or discussed, including in substantially concurrent or in reverse order, depending on the functionality involved. Further, more or fewer steps, blocks and/or functions may be used with any of the message flow diagrams, scenarios, and flow charts discussed herein, and these message flow diagrams, scenarios, and flow charts may be combined with one another, in part or in whole.

A step or block that represents a processing of information may correspond to circuitry that can be configured to perform the specific logical functions of a herein-described method or technique. Alternatively or additionally, a step or block that represents a processing of information may correspond to a module, a segment, or a portion of program code (including related data). The program code may include one or more instructions executable by a processor for implementing specific logical functions or actions in the method or technique. The program code and/or related data may be stored on any type of computer-readable medium, such as a storage device, including a disk drive, a hard drive, or other storage media.

The computer-readable medium may also include non-transitory computer-readable media such as computer-readable media that stores data for short periods of time like register memory, processor cache, and/or random access memory (RAM). The computer-readable media may also include non-transitory computer-readable media that stores program code and/or data for longer periods of time, such as secondary or persistent long term storage, like read only memory (ROM), optical or magnetic disks, and/or compact-disc read only memory (CD-ROM), for example. The computer-readable media may also be any other volatile or non-volatile storage systems. A computer-readable medium may be considered a computer-readable storage medium, for example, or a tangible storage device.

Moreover, a step or block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

We claim:
1. A microneedle array comprising:
a plurality of microneedles;
a backing to which each microneedle of the plurality of microneedles is coupled; and
a plurality of fibers, wherein the plurality of fibers are disposed within an entire internal volume of the plurality of microneedles and the plurality of fibers do not extend into the backing, and wherein the plurality of fibers are electrospun with one or more excipients incorporated in the plurality of fibers to thereby increase a porosity of the plurality of fibers, wherein at least one of a small molecule, a biologic, an antibody, RNA, DNA, or other pharmaceutically active substance is disposed within the plurality of fibers, and wherein at least one of a small molecule, a biologic, an antibody, RNA, DNA, or other pharmaceutically active substance is disposed within a material of the plurality of microneedles that is not the plurality of fibers.

2. The microneedle array of claim 1, wherein each microneedle of the plurality of microneedles has a failure force exceeding 0.04 N.

3. The microneedle array of claim 1, wherein a first pharmaceutically active substance is disposed within the plurality of fibers, wherein a second pharmaceutically active substance is disposed within a material of the plurality of microneedles that is not the plurality of fibers, and wherein the first pharmaceutically active substance is different than the second pharmaceutically active substance.

4. The microneedle array of claim 1, wherein the plurality of microneedles comprises a surface area of 4.2 cm$^2$.

5. The microneedle array of claim 1, wherein each of the plurality of microneedles have a diameter of 350 μm and a height of 800 μm.

6. The microneedle array of claim 1, wherein each of the plurality of microneedles are spaced 1 mm apart center-to-center.

7. The microneedle array of claim 1, wherein the plurality of fibers include polyvinyl alcohol (PVA), polycaprolactone (PCL), or poly(lactic-co-glycolic acid) (PLGA).

8. The microneedle array of claim 1, wherein the plurality of microneedles include poly(acrylic acid) (PAA).

\* \* \* \* \*